(12) United States Patent
Lücking et al.

(10) Patent No.: US 8,802,686 B2
(45) Date of Patent: *Aug. 12, 2014

(54) SULFONE-SUBSTITUTED ANILINOPYRIMIDINE DERIVATIVES AS CDK INHIBITORS, THE PRODUCTION THEREOF, AND USE AS A MEDICINE

(75) Inventors: Ulrich Lücking, Berlin (DE); Gerhard Siemeister, Berlin (DE); Philip Lienau, Berlin (DE); Rolf Jautelat, Haan (DE); Julia Schulze, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 377 days.

This patent is subject to a terminal disclaimer.

(21) Appl. No.: 13/125,144

(22) PCT Filed: Oct. 8, 2009

(86) PCT No.: PCT/EP2009/007213
§ 371 (c)(1),
(2), (4) Date: Jun. 24, 2011

(87) PCT Pub. No.: WO2010/046034
PCT Pub. Date: Apr. 29, 2010

(65) Prior Publication Data
US 2011/0251222 A1    Oct. 13, 2011

(30) Foreign Application Priority Data
Oct. 21, 2008 (EP) .................................. 08167115

(51) Int. Cl.
*A61K 31/505* (2006.01)
*C07D 239/24* (2006.01)

(52) U.S. Cl.
USPC ............................ 514/269; 514/275; 544/323

(58) Field of Classification Search
USPC .................... 514/269, 275; 544/323
See application file for complete search history.

(56) References Cited

U.S. PATENT DOCUMENTS

2004/0198757 A1   10/2004   Newcombe et al.
2011/0251222 A1 *  10/2011   Lucking et al. ............... 514/275

FOREIGN PATENT DOCUMENTS

| WO | WO 02/096887 A1 | 12/2002 |
| WO | WO 03/032997 A1 | 4/2003 |
| WO | WO 2005/037800 A1 | 4/2005 |
| WO | WO 2008/107096 A1 | 9/2008 |

OTHER PUBLICATIONS

Truce et al., Sulfones and Sulfoximines.*
International Search Report of PCT/EP2009/007213 (Jan. 8, 2010).

* cited by examiner

*Primary Examiner* — Kamal Saeed
*Assistant Examiner* — Ebenezer O Sackey

(57) ABSTRACT

The invention relates to sulphone-substituted anilinopyrimidine derivatives of the formula (I),

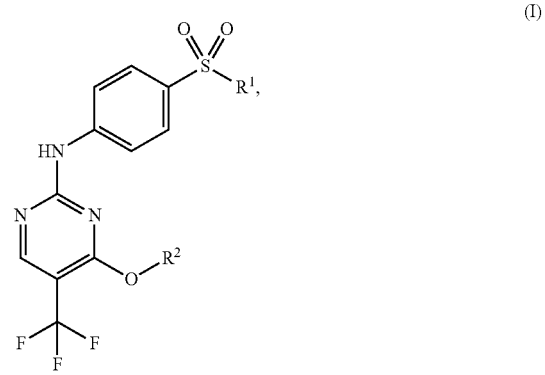

to its preparation processes, and to its use as medicament for treating various diseases.

12 Claims, No Drawings

SULFONE-SUBSTITUTED ANILINOPYRIMIDINE DERIVATIVES AS CDK INHIBITORS, THE PRODUCTION THEREOF, AND USE AS A MEDICINE

The present invention relates to sulphone-substituted anilinopyrimidine derivatives, to processes for their preparation, and to their use as medicament for treating various diseases.

The cyclin-dependent kinases (CDKs) are a family of enzymes which plays an important role in the regulation of the cell cycle and therefore represents a particularly interesting target for the development of small inhibitory molecules. Selective inhibitors of the CDKs can be used for the treatment of cancer or other diseases caused by disturbances of cell proliferation.

Pyrimidines and analogues have already been described as active ingredients, such as, for example, the 2-anilinopyrimidines as fungicides (DE4029650) or substituted pyrimidine derivatives for treating neurological or neurodegenerative diseases (WO 99/19305). Very diverse pyrimidine derivatives are described as CDK inhibitors, for example 2-amino-4-substituted pyrimidines (WO 01/14375), purines (WO 99/02162), 5-cyanopyrimidines (WO 02/04429), anilinopyrimidines (WO 00/12486) and 2-hydroxy-3-N,N-dimethylaminopropoxypyrimidines (WO 00/39101).

In particular, in WO 02/09688 and WO 03/076437, pyrimidine derivatives have been disclosed which have inhibitory effects with respect to CDKs.

WO 2005/037800 discloses open sulphoximine-substituted anilinopyrimidine derivatives as inhibitors of the cyclin-dependent kinases. By way of example, structures are given which are either unsubstituted, or substituted with halogen, especially with bromine, in the 5-position of the pyrimidine. None of the specifically disclosed structures has a 5-trifluoromethyl substituent.

WO 2003/032997 discloses sulphone-substituted anilinopyrimidines, for which, however, a nitrogen-containing radical is obligatorily provided in position 4 of the pyrimidine.

The specifically disclosed structure coming closest to the structures according to the invention is structure 692 of Example 1.

Proceeding from this prior art, the object of the present invention is to provide compounds which inhibit the activity of the cyclin-dependent kinases to a greater extent than the compounds of the prior art. Furthermore, the compounds should be more selective towards the inhibition of the VEGF receptor kinase-2 (VEGF-$R^2$). The compounds should be readily permeable in the absorptive direction and not very permeable in the efflux direction. In particular, the compounds should also have a strongly antiproliferative effect in chemotherapy-resistant tumour cells.

It has now been found that compounds of the general formula (I)

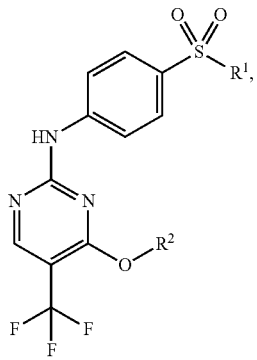

(I)

in which $R^1$ is a $C_1$-$C_6$-alkyl, $C_2$-$C_6$-alkenyl, $C_2$-$C_6$-alkynyl radical or a $C_3$-$C_7$-cycloalkyl or phenyl ring, in each case optionally substituted one or more times, identically or differently, with hydroxy, —$NR^3R^4$, cyano, halogen, —$CF_3$, $C_1$-$C_6$-alkoxy, —$OCF_3$ and/or $C_1$-$C_6$-alkyl, and $R^2$ is a $C_1$-$C_{10}$-alkyl, $C_3$-$C_{10}$-alkenyl or $C_3$-$C_{10}$-alkynyl radical or a $C_3$-$C_7$-cycloalkyl ring, in each case optionally substituted one or more times, identically or differently, with a) halogen, hydroxy, —$NR^3R^4$, cyano, —$CF_3$, —$OCF_3$, and/or b) $C_1$-$C_6$-alkoxy, $C_1$-$C_6$-alkyl, $C_2$-$C_6$-alkenyl, $C_2$-$C_6$-alkynyl, or $C_3$-$C_8$-cycloalkyl, —O—$CH_2$-phenyl, $C_n$-alkoxycarbonyl, in each case optionally substituted themselves one or more times, identically or differently, with halogen, hydroxy, a $C_1$-$C_6$-alkyl, $C_1$-$C_6$-alkoxy, —$NR^3R^4$, —$CF_3$ and/or —$OCF_3$, and $R^3$ and $R^4$ independently of one another, are hydrogen and/or a $C_1$-$C_6$-alkyl radical, $C_2$-$C_6$-alkenyl radical, $C_3$-$C_8$-cycloalkyl and/or phenyl ring, a heterocyclyl ring having 3 to 8 ring atoms and/or a monocyclic heteroaryl ring, optionally substituted one or more times, identically or differently, with hydroxy, —$NR^5R^6$, cyano, halogen, —$CF_3$, $C_1$-$C_6$-alkoxy and/or —$OCF_3$, or $R^3$ and $R^4$ together with the nitrogen atom, form a 5- to 7-membered ring which, optionally, in addition to the nitrogen atom, contains one or two further heteroatoms and which may be substituted one or more times, identically or differently, with hydroxy, —$NR^5R^6$, cyano, halogen, —$CF_3$, $C_1$-$C_6$-alkoxy and/or —$OCF_3$, and $R^5$ and $R^6$ independently of one another, are hydrogen or a $C_1$-$C_6$-alkyl radical, which is optionally substituted one or more times, identically or differently, with hydroxy, cyano, halogen, —$CF_3$, $C_1$-$C_6$-alkoxy and/or —$OCF_3$, and salts, diastereomers and enantiomers thereof.

The invention is based on the following definitions:

$C_n$-Alkyl:

Monovalent, straight-chain or branched, saturated hydrocarbon radical having n carbon atoms.

A $C_1$-$C_6$-alkyl radical includes, inter alia, for example: methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, 1,2-dimethylbutyl.

Preference is given to a methyl, ethyl, propyl or isopropyl radical.

$C_n$-Alkenyl:

Monovalent, straight-chain or branched hydrocarbon radical having n carbon atoms and at least one double bond.

A $C_2$-$C_{10}$-alkenyl radical includes, inter alia, for example: vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)pent-1-enyl, (Z)pent-1-enyl, hex-5-enyl, (E)-hex-4-enyl, (Z)-hen-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl(Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)ethenyl.

Preference is given to a vinyl or allyl radical.

$C_n$-Alkynyl:

Monovalent, straight-chain or branched hydrocarbon radical having n carbon atoms and at least one triple bond.

A $C_2$-$C_{10}$-alkynyl radical includes, inter alia, for example: ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl or 3,3-dimethylbut-1-ynyl.

Preference is given to an ethynyl, prop-1-ynyl or prop-2-ynyl radical.

$C_n$-Cycloalkyl:

Monovalent, cyclic hydrocarbon ring having n carbon atoms.

$C_3$-$C_7$-cycloalkyl ring includes:
cyclopropyl, cyclobutyl, cyclopentyl, cyclohexyl and cycloheptyl.

Preference is given to a cyclopropyl, cyclopentyl or a cyclohexyl ring.

$C_n$-Alkoxy:

Straight-chain or branched $C_n$-alkyl ether radial of the formula —OR where R=$C_n$-alkyl.

$C_n$-Alkoxycarbonyl $C_n$-alkoxycarbonyl is the group —C(O)—O—$C_n$-alkyl.

As a rule, n is 1 to 6, preferably 1 to 4, and particularly preferably 1 to 3.

By way of example and preferably, mention may be made of:
methoxycarbonyl, ethoxycarbonyl, propoxycarbonyl, isopropoxycarbonyl, tert-butoxycarbonyl, n-pentoxy-carbonyl and n-hexoxycarbonyl.

Halogen

The term halogen includes fluorine, chlorine, bromine and iodine.

Preference is given to fluorine.

In the general formula (I), $R^1$ can be:
a $C_1$-$C_6$-alkyl, $C_2$-$C_6$-alkenyl, $C_2$-$C_6$-alkynyl radical or a $C_3$-$C_7$-cycloalkyl or phenyl ring, in each case optionally substituted one or more times, identically or differently, with hydroxy, —$NR^3R^4$, cyano, halogen, —$CF_3$, $C_1$-$C_6$-alkoxy, —$OCF_3$ and/or $C_1$-$C_6$-alkyl.

Preferably, $R^1$ is a $C_1$-$C_6$-alkyl, $C_2$-$C_6$-alkenyl, $C_2$-$C_6$-alkynyl radical or a $C_3$-$C_7$-cycloalkyl or phenyl ring, in each case optionally substituted one or more times, identically or differently, with hydroxy, cyano, halogen, —$CF_2$, $C_1$-$C_6$-alkoxy, —$OCF_2$ and/or $C_1$-$C_6$-alkyl.

More preferably, $R^1$ is a $C_1$-$C_6$-alkyl or $C_2$-$C_6$-alkenyl radical or a $C_3$-$C_7$-cycloalkyl or phenyl ring, in each case optionally substituted one or more times, identically or differently, with hydroxy, cyano, halogen and/or $C_1$-$C_6$-alkyl.

More preferably, $R^1$ is a $C_1$-$C_4$-alkyl or $C_2$-$C_4$-alkenyl radical or a $C_3$-$C_5$-cycloalkyl or phenyl ring, in each case optionally substituted one or more times, identically or differently, with hydroxy, cyano, halogen and/or $C_1$-$C_3$-alkyl.

Extraordinarily preferably, $R^1$ is a methyl group or a cyclopropyl ring. In the general formula (I), $R^1$ may be:
a $C_1$-$C_{10}$-alkyl, $C_3$-$C_{10}$-alkenyl or $C_3$-$C_{10}$-alkynyl radical or a $C_3$-$C_7$-cycloalkyl ring, in each case optionally substituted one or more times, identically or differently, with a) halogen, hydroxy, —$NR^3R^4$, cyano, —$CF_2$, —$OCF_2$, and/or b) $C_1$-$C_6$-alkoxy, $C_1$-$C_6$-alkyl, $C_2$-$C_6$-alkenyl, $C_2$-$C_6$-alkynyl, or $C_3$-$C_8$-cycloalkyl, —O—$CH_2$-phenyl, $C_n$-alkoxycarbonyl, in each case optionally substituted themselves one or more times, identically or differently, with halogen, hydroxy, a $C_1$-$C_6$-alkyl, $C_1$-$C_6$-alkoxy, —$NR^3R^4$, —$CF_3$ and/or —$OCF_2$.

Preferably, $R^2$ is a $C_1$-$C_{10}$-alkyl, $C_3$-$C_{10}$-alkenyl or $C_3$-$C_{10}$-alkynyl radical or a $C_3$-$C_7$-cycloalkyl ring, in each case optionally substituted one or more times, identically or differently, with halogen, hydroxy, cyano, —$CF_3$, —$OCF_3$, and/or $C_1$-$C_6$-alkoxy, $C_1$-$C_6$-alkyl, in each case optionally substituted themselves one or more times, identically or differently, with halogen or hydroxy.

More preferably, $R^2$ is a $C_2$-$C_6$-alkyl, $C_3$-$C_6$-alkenyl or $C_7$-$C_6$-alkynyl radical or a $C_3$-$C_7$-cycloalkyl ring, which is optionally substituted one or more times with hydroxy, halogen, —$CF_3$ and/or $C_1$-$C_3$-alkoxy.

Particularly preferably, $R^2$ is the group with the part formula ($I_{-R}^2$),

$$(I_{-R^2})$$

in which
$R^a$ is a methyl, ethyl, propyl or isopropyl group, and
$R^b$ and $R^c$ independently of one another, are hydrogen, a methyl or ethyl group.

Formula (Ia) summarizes this group of compounds.

Preferably, $R^a$ and $R^b$ are a methyl group, and $R^c$ is hydrogen or a methyl group.

In the general formula (I), $R^3$ and $R^4$, independently of one another, may be:
hydrogen and/or a $C_1$-$C_6$-alkyl radical, $C_2$-$C_6$-alkenyl radical, $C_3$-$C_8$-cycloalkyl and/or phenyl ring, a heterocycle ring having 3 to 8 ring atoms and/or a monocyclic heteroaryl ring, optionally substituted one or more times, identically or differently, with hydroxy, —$NR^5R^6$, cyano, halogen, —$CF_3$, $C_1$-$C_6$-alkoxy and/or —$OCF_3$,
or
$R^3$ and $R^4$, together with the nitrogen atom, form a 5- to 7-membered ring which, optionally, in addition to the nitrogen atom, contains one or two further heteroatoms and which may be substituted one or more times, identically or differently, with hydroxy, —$NR^5R^6$, cyano, halogen, —$CF_3$, $C_1$-$C_6$-alkoxy and/or —$OCF_3$.

Preferably, $R^3$ and $R^4$, independently of one another, are:
hydrogen and/or a $C_1$-$C_4$-alkyl radical, $C_3$-$C_6$-alkenyl radical, $C_3$-$C_6$-cycloalkyl and/or phenyl radical, a heterocyclyl ring having 5 or 6 ring atoms and/or a monocyclic heteroaryl ring, optionally substituted one or more times, identically or differently, with hydroxy, —$NR^5R^6$, cyano, halogen, —$CF_3$, $C_1$-$C_6$-alkoxy and/or —$OCF_3$,
or
$R^3$ and $R^4$, together with the nitrogen atom, form a 5- to 7-membered ring which, optionally, in addition to the nitrogen atom, contains one further heteroatom and which may be substituted one or more times, identically or differently, with hydroxy, —$NR^5R^6$, cyano, halogen, —$CF_3$, $C_1$-$C_6$-alkoxy and/or —$OCF_3$.

More preferably, $R^3$ and $R^4$, independently of one another, are hydrogen and/or a $C_1$-$C_6$-alkyl radical, $C_3$-$C_8$-cycloalkyl and/or phenyl ring, optionally substituted one or more times, identically or differently, with hydroxy, cyano, halogen, —$CF_3$, $C_1$-$C_6$-alkoxy and/or —$OCF_3$.

In the general formula (I), $R^5$ and $R^6$, independently of one another, may be: hydrogen or a $C_1$-$C_6$-alkyl radical, which is optionally substituted one or more times, identically or differently, with hydroxy, cyano, halogen, —$CF_3$, $C_1$-$C_6$-alkoxy and/or —$OCF_3$.

Preferably, $R^5$ and $R^6$, independently of one another, are hydrogen and/or a $C_1$-$C_3$-alkyl radical.

A preferred subgroup is formed by compounds of the general formula (I), in which
$R^1$ is a $C_1$-$C_6$-alkyl, $C_2$-$C_6$-alkenyl, $C_2$-$C_6$-alkynyl radical or a $C_3$-$C_7$-cycloalkyl or phenyl radical, in each case optionally substituted one or more times, identically or differently, with hydroxy, cyano, halogen, —$CF_3$, $C_1$-$C_6$-alkoxy, —$OCF_3$ and/or $C_1$-$C_6$-alkyl, and
$R^2$ is a $C_1$-$C_{10}$-alkyl, $C_3$-$C_{10}$-alkenyl or $C_3$-$C_{10}$-alkynyl radical or a $C_3$-$C_7$-cycloalkyl ring, in each case optionally substituted one or more times, identically or differently, with halogen, hydroxy, cyano, —$CF_3$, —$OCF_3$ and/or $C_1$-$C_6$-alkoxy, $C_1$-$C_6$-alkyl, in each case optionally substituted themselves one or more times, identically or differently, with halogen or hydroxy,
and salts, diastereomers and enantiomers thereof.

A more preferred subgroup is formed by compounds of the general formula (I) in which
$R^1$ is a $C_1$-$C_6$-alkyl or $C_2$-$C_6$-alkenyl radical or a $C_3$-$C_7$-cycloalkyl or phenyl ring, in each case optionally substituted one or more times, identically or differently, with hydroxy, cyano, halogen and/or $C_1$-$C_6$-alkyl, and
$R^2$ is a $C_2$-$C_6$-alkyl, $C_3$-$C_6$-alkenyl or $C_3$-$C_6$-alkynyl radical or a $C_3$-$C_7$-cycloalkyl radical, which is optionally substituted one or more times with hydroxy, halogen, —$CF_3$ and/or $C_1$-$C_3$-alkoxy, and salts, diastereomers and enantiomers thereof.

A particularly preferred subgroup is formed by compounds of the general formula (Ia)

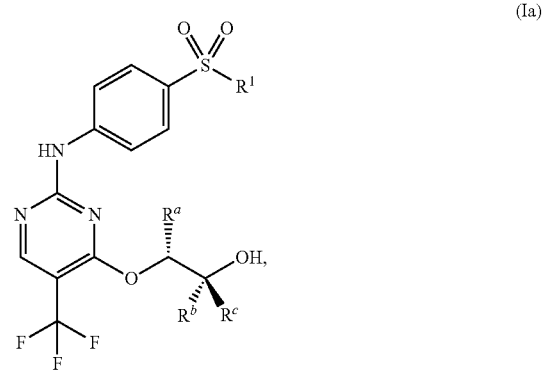

(Ia)

in which
$R^1$ is a $C_1$-$C_4$-alkyl or $C_2$-$C_4$-alkenyl radical or a $C_3$-$C_5$-cycloalkyl or phenyl ring, in each case optionally substituted one or more times, identically or differently, with hydroxy, cyano, halogen and/or $C_1$-$C_3$-alkyl, and
$R^a$ is a methyl, ethyl, propyl or isopropyl group, and
$R^b$ and $R^c$ independently of one another, are hydrogen, a methyl or ethyl group,
and salts, diastereomers and enantiomers thereof.

A preferred subgroup of the compounds of the general formula (Ia) is formed by the group of compounds in which
$R^1$ is a methyl group or a cyclopropyl ring, and
$R^a$ and $R^b$ is a methyl group, and
$R^c$ is hydrogen or a methyl group,
and salts, diastereomers and enantiomers thereof.

The compounds according to the invention are suitable for treating
cancer, such as solid tumours, tumour metastases, and haematological tumours, in particular:
head and neck tumours; lung and bronchial tumours; gastrointestinal tumours, such as e.g. gastric carcinoma, colorectal carcinoma, pancreatic carcinoma, hepatocellular carcinoma; endocrine active tumours; breast carcinomas and gynaecological tumours; urogenital tumours, such as e.g. kidney cell carcinoma, urinal bladder carcinoma, prostate carcinoma; skin tumours; sarcomas; leukaemias and lymphomas.
viral diseases, and
cardiovascular diseases such as stenoses, arterioscleroses and restenoses, stent-induced restenoses.

Formulation of the compounds according to the invention to give pharmaceutical preparations takes place in a manner known per se, by converting the active ingredient or the active ingredients with the excipients customary in pharmaceutical technology to the desired application form.

Excipients which can be used here are, for example, carrier substances, fillers, disintegrants, binders, humectants, glidants, adsorbents and absorbents, diluents, solvents, cosolvents, emulsifiers, solubility promoters, taste correctives, colorants, preservatives, stabilizers, wetting agents, salts for altering the osmotic pressure or buffers.

In this connection, reference is made to Remington's Pharmaceutical Science, 15th ed. Mack Publishing Company, East Pennsylvania (1980).

The pharmaceutical formulations can be
in solid form, for example as tablets, sugar-coated tablets, pills, suppositories, capsules, transdermal systems or in semi-solid form, for example as ointments, creams, gels, suppositories, emulsions, or
in liquid form, for example as solutions, tinctures, suspensions or emulsions.

Excipients for the purposes of the invention may be, for example, salts, saccharides (mono-, di-, tri-, oligo- and/or polysaccharides), proteins, amino acids, peptides, fats, waxes, oils, hydrocarbons and derivatives thereof, it being possible for the excipients to be of natural origin or to be obtained synthetically or partially synthetically.

For oral or peroral application, tablets, sugar-coated tablets, capsules, pills, powders, granules, pastilles, suspensions, emulsions or solutions, in particular, are suitable.

For parenteral application, suspensions, emulsions and primarily solutions, in particular, are suitable.

PREPARATION OF THE COMPOUNDS ACCORDING TO THE INVENTION

The examples below illustrate the preparation of the compounds according to the invention without limiting the scope of the claimed compounds to these examples.

The compounds according to the invention can be prepared by a process which is characterized by the following steps:

$a_1$) functionalization of the 4-position of 2,4-dichloro-5-iodopyrimidine (1) by reaction with an alcohol of the formula (2) to form an intermediate of the formula (3),

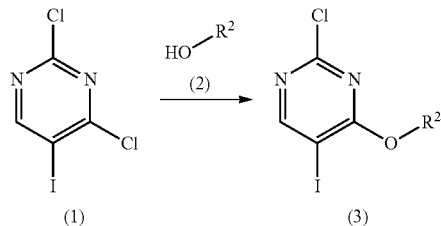

and subsequent reaction of intermediate (3) to form the 5-CF$_3$ intermediate (4)

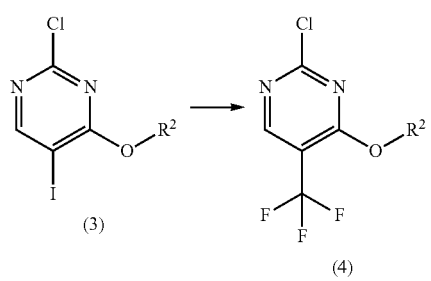

or alternatively $a_2$) direct reaction of 2,4-dichloro-5-trimethylpyrimidine (5) and an alcohol of the formula (2) to form the 5-CF$_3$ intermediate (4),

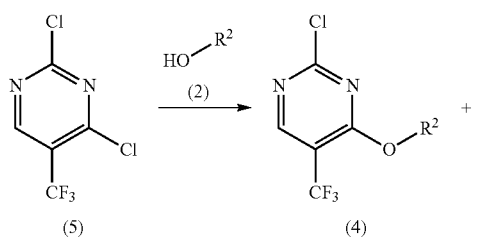

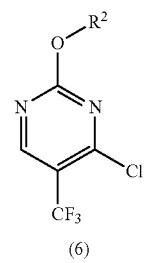

b) oxidation of a thioether of the formula (7) to give the sulphone of the formula (8),

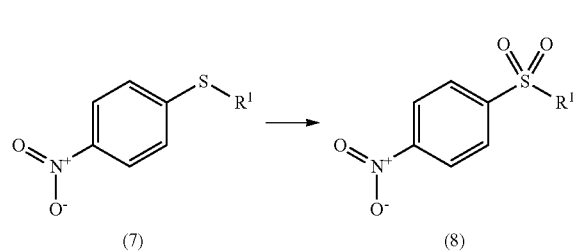

c) reduction of the compound of the formula (8) to a compound of the formula (9),

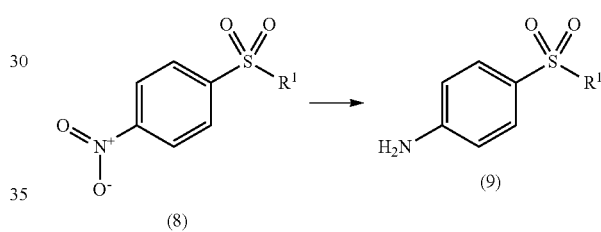

d) coupling of the compounds of the formula (4) and (9)

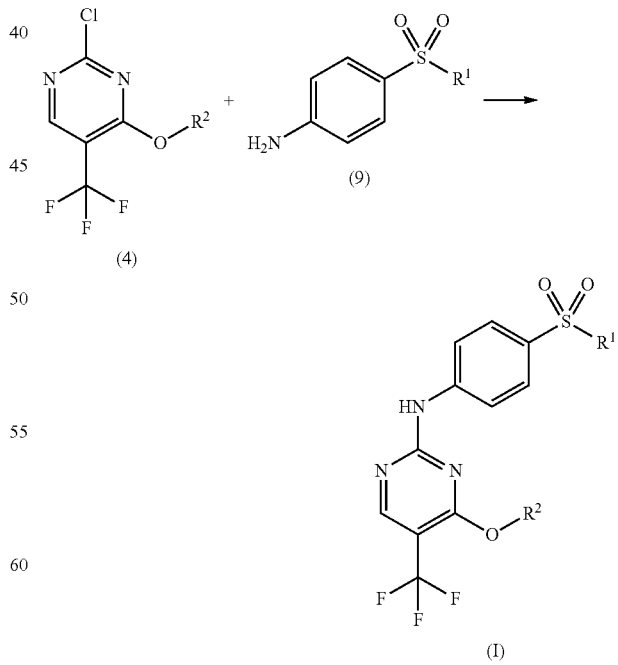

The preparation of the compounds according to the invention optionally requires the introduction and subsequent cleaving off of protective groups (see e.g.: P. J. Kocienski, Protecting Groups, Georg Thieme Verlag Stuttgart, N.Y., 1994) such as e.g. in the side chain of the 4-position.

Process Step $a_1$)

The reaction of 2,4-dichloro-5-iodopyrimidine (1) with an alcohol of the formula (2) under basic conditions permits the synthesis of a product of the formula (3) (see e.g.: (a) U. Lucking et al., WO 2007/071455). Of particular suitability for the synthesis is the described use of sodium hydride.

For replacing a halogen with a trifluoromethyl group in a nitrogen-containing heteroaromatic, various methods are in principle available (see e.g.: a) G. E. Carr, R. D. Chambers, T. F. Holmes, J. Chem. Soc. Perkin Trans. 1, 1988, 921; b) F. Cottet, M. Schlosser, Eur. J. Org. Chem. 2002, 327; c) F. G. Njoroge et al., J. Med. Chem. 1997, 40, 4290).

Of particular suitability for replacing the iodine in the 5-position of the pyrimidine (3) with a $CF_3$ group to form a compound of the formula (4) is the described use of copper(I) iodide, potassium fluoride and (trifluoromethyl)trimethylsilane in N-methyl-2-pyrrolidinone and THF.

Process Step $a_2$)

The reaction of 2,4-dichloro-5-trifluoromethylpyrimidine (5) with an alcohol of the formula (2) under basic conditions permits the synthesis of the products (4) and (6). The regioisomers can generally be separated by chromatography (see e.g.: (a) T. M. Caldwell et al., WO 2006/081388, p. 50, Example 1, D). Of particular suitability for the synthesis is the described use of sodium hydride.

Process Step b)

A compound of the formula (7) is oxidized to the sulphone of the formula (8). For converting a thioether to a sulphone, numerous methods are available, e.g. using the oxidizing agent hydrogen peroxide or potassium permanganate. Of particular suitability for the synthesis of compounds of the formula (8) is the described use of metachloroperbenzoic acid (MCPBA).

Process Step c)

For the subsequent reduction of the aromatic nitro group to a compound of the formula (9), a series of reaction conditions are in principle available (see e.g.: R. C. Larock, *Comprehensive Organic Transformations*, VCH, New York, 1989, 411). Of particular suitability is, for example, the described hydrogenation using Raney nickel in THF.

Process Step d)

A compound of the formula (4) can be reacted with an aniline of the formula (9) to give a compound of the formula (I) (see e.g.: (a) J. Bryant et al., WO 2004/048343).

GENERAL COMMENTS

All reactions with oxidation-sensitive or hydrolysis-sensitive compounds were carried out under argon and with dried solvents.

The substances were named using the program Autonom 2000 Name, which is implemented in MDL ISIS Draw.

ABBREVIATIONS

| Abbreviation | Meaning |
|---|---|
| Ac | Acetyl |
| Aloc | Allyloxycarbonyl |
| Boc | tert-Butyloxycarbonyl |
| BOM | Benzyloxymethyl |
| br | Broad |
| CI | Chemical ionization |
| d | Doublet |
| dd | Doublet of doublet |
| DCM | Dichloromethane |
| DMF | N,N-dimethylformamide |
| DMSO | Dimethyl sulphoxide |
| ESI | Electrospray ionization |
| HPLC | High performance liquid chromatography |
| m | Multiplet |
| MEM | (2-Methoxyethoxy)methyl |
| MOM | Methoxymethyl |
| MS | Mass spectrometry |
| MTM | Methylthiomethyl |
| NMP | N-Methyl-2-pyrrolidinone |
| NMR | Nuclear magnetic resonance spectroscopy: chemical shift (δ) is given in ppm |
| Pg | Protective group comprising groups such as e.g. TMS, TES, TBDMS, TDBPS, TIPS, benzyl, PMB, trityl, allyl, Aloc, MOM, MTM, MEM, BOM, SEM, THP |
| PMB | p-Methoxybenzyl |
| q | Quartet |
| s | Singlet |
| SEM | β-(Trimethylsilyl)ethoxymethyl |
| TBDMS | tert-Butylsilyldimethyl |
| TBDPS | tert-Butylsilyldiphenyl |
| TEA | Triethylamine |
| TES | Triethylsilyl |
| THF | Tetrahydrofuran |
| THP | Tetrahydropyranyl |
| TIPS | Triisopropyl |
| TMS | Trimethylsilyl |
| tr | Triplet |

EXAMPLE 1

(2R,3R)-3-[2-(4-Cyclopropanesulphonylphenylamino)-5-trifluoromethylpyrimidin-4-yloxy]butan-2-ol

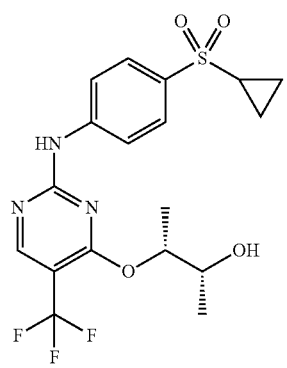 [SMILES: C[C@@H](O)[C@@H](C)Oc1nc(Nc2ccc(S(=O)(=O)C3CC3)cc2)ncc1C(F)(F)F]

1a) Preparation of the Intermediates

Compound 1.1

1-Cyclopropylsulphanyl-4-nitrobenzene

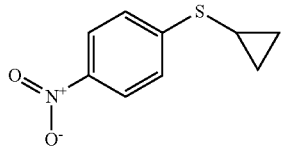 [SMILES: O=[N+]([O-])c1ccc(SC2CC2)cc1]

A 4% strength solution of 3.00 g (40.5 mmol) of cyclopropanethiol (preparation according to: E. Block et al., *J. Am. Chem. Soc.* 1992, 114, 3492) in THF/diethyl ether (1:1) was admixed in portions with 1.78 g (44.6 mmol) of sodium hydride (60%) and stirred for 30 minutes at room temperature. The portionwise addition of 6.00 g (38.7 mmol) of 1-fluoro-4-nitrobenzene was then carried out. The mixture was stirred at 40° C. for 2 hours. After cooling, the mixture was added to water and extracted (3×) with benzene. The combined organic phases were concentrated by evaporation and the residue was purified chromatographically (hexane/ethyl acetate 95:5). This gave 4.6 g (23.6 mmol; yield: 61%) of the product.

$^1$H NMR (400 MHz, DMSO): δ=8.12 (m, 2H), 7.54 (m, 2H), 2.35 (m, 1H), 1.16 (m, 2H), 0.61 (m, 2H).

Compound 1.2

1-Cyclopropanesulphonyl-4-nitrobenzene

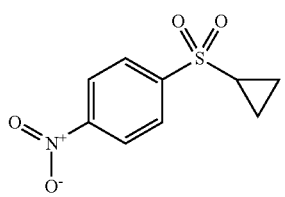 [SMILES: O=[N+]([O-])c1ccc(S(=O)(=O)C2CC2)cc1]

A solution of 1.00 g (5.12 mmol) of 1-cyclopropylsulphanyl-4-nitrobenzene in 120 ml of DCM was admixed at 0° C. with 2.3 g of meta-chloroperbenzoic acid (max. 77%) and then stirred for 4.5 hours at room temperature. The mixture was added, with stirring, to a saturated sodium hydrogen carbonate solution. The organic phase was filtered through a Whatman filter and concentrated by evaporation. The resulting residue was purified chromatographically (DCM/MeOH 95:5). This gave 1.07 g (4.70 mmol; yield: 92%) of the product.

$^1$H NMR (400 MHz, DMSO): δ=8.41 (m, 2H), 8.15 (m, 2H), 2.98 (m, 1H), 1.11 (m, 4 h).

Compound 1.3

4-Cyclopropanesulphonylphenylamine

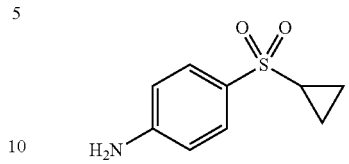

A solution of 1.60 g (7.0 mmol) of 1-cyclopropanesulphonyl-4-nitrobenzene in 50 ml of ethanol and 50 ml of THF was admixed with 3.2 g of Raney nickel (50% moisture) and hydrogenated for 1.5 hours under atmospheric pressure at 0° C. The mixture was filtered and concentrated by evaporation. This gave 1.28 g (6.5 mmol; yield: 92%) of the product.

$^1$H NMR (400 MHz, DMSO): δ=7.41 (m, 2H), 6.60 (m, 2H), 6.05 (br, 2H), 2.58 (m, 1H), 0.92 (m, 4H)
MS: 198 (ESI+).

Compound 1.4

(2R,3R)-3-benzyloxybutan-2-ol

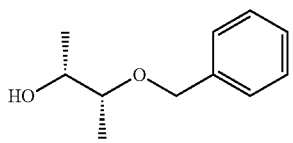

A solution of 4.0 g (44.4 mmol) of (2R,3R)-butane-2,3-diol in 300 ml of THF was admixed at room temperature with 5.0 g (44.6 mmol) of potassium tert-butylate and the mixture was refluxed for 15 minutes. The mixture was cooled to ca. 50° C. and admixed with 5.3 ml (44.6 mmol) of benzyl bromide. The mixture was refluxed for 3 hours, then stirred overnight at room temperature. The mixture was diluted with ethyl acetate and sodium chloride solution and then washed with 1N hydrogen chloride solution (1×) and sodium chloride solution (2×). The organic phase was dried (Na$_2$SO$_4$), filtered and concentrated by evaporation. The resulting residue was purified chromatographically (hexane/ethyl acetate 1:1). This gave 3.4 g (18.9 mmol; yield: 43%) of the product.

$^1$H NMR (400 MHz, DMSO): δ=7.35 (m, 4H), 7.28 (m, 1H), 4.52 (m, 3H), 3.67 (m, 1H), 3.37 (m, 1H), 1.05 (d, 3H), 1.01 (d, 3H).

Compound 1.5

4-((1R,2R)-2-benzyloxy-1-methylpropoxy)-2-chloro-5-iodopyrimidine

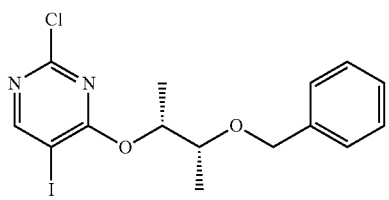 [SMILES: C[C@@H](OCc1ccccc1)[C@@H](C)Oc1nc(Cl)ncc1I]

8.55 g (47.4 mmol) of (2R,3R)-3-benzyloxybutan-2-ol in 56 ml of diethyl ether were admixed at 0° C. with stirring in portions with 2.07 g of sodium hydride (55%). After 10 minutes, the ice bath was removed and the mixture was stirred for a further 3 minutes at room temperature. The suspension formed was added at 0° C. to a solution of 6.52 g (23.7 mmol) of 2,4-dichloro-5-iodopyrimidine in 65 ml of acetonitrile. The mixture was stirred for 4 hours at 40° C. and then admixed with dilute sodium chloride solution. Extraction was carried out with ethyl acetate (2×). The combined organic phases were dried (Na₂SO₄), filtered and concentrated by evaporation. The resulting residue was purified chromatographically (hexane/ethyl acetate 4:1). This gave 4.12 g (9.8 mmol; yield: 41%) of the product.

¹H NMR (400 MHz, DMSO): δ=8.78 (s, 1H), 7.29 (m, 5H), 5.27 (m, 1H), 4.64 (d, 1H), 4.53 (d, 1H), 3.73 (m, 1H), 1.30 (d, 3H), 1.19 (d, 3H).

Compound 1.6

4-((1R,2R)-2-benzyloxy-1-methylpropoxy)-2-chloro-5-trifluoromethylpyrimidine

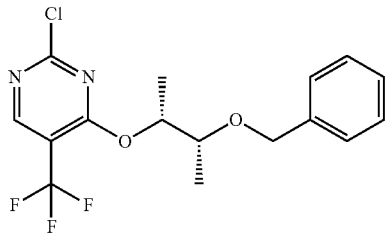 [SMILES: C[C@@H](OCc1ccccc1)[C@@H](C)Oc1nc(Cl)ncc1C(F)(F)F]

A solution of 4.66 g (11.1 mmol) of 4-((1R,2R)-2-benzyloxy-1-methylpropoxy)-2-chloro-5-iodopyrimidine in 15.8 ml of NMP and 15.8 ml of THF was admixed at room temperature with stirring with 3.82 g (20.0 mmol) of copper(I) iodide, 0.97 g (16.7 mmol) of potassium fluoride and 2.47 ml (16.7 mmol) of (trifluoromethyl)trimethylsilane. The mixture was stirred for 5.5 hours at 80° C. After cooling, the mixture was added to dilute sodium chloride solution and extracted (2×) with ethyl acetate. The combined organic phases were dried (Na₂SO₄), filtered and concentrated by evaporation. The resulting residue was purified chromatographically (hexane/ethyl acetate 4:1). This gave 2.17 g (6.0 mmol; yield: 54%) of the product.

¹H NMR (400 MHz, DMSO): δ=8.81 (s, 1H), 7.21 (m, 5H), 5.40 (m, 1H), 4.57 (d, 1H), 4.42 (d, 1H), 3.70 (m, 1H), 1.28 (d, 3H), 1.13 (d, 3H).

Alternatively, compound 1.6 was also prepared by the following procedure:

A solution of 5.00 g (23.0 mmol) of 2,4-dichloro-5-trifluoromethylpyrimidine and 5.40 g (30.0 mmol) of (2R,3R)-3-benzyloxybutan-2-ol in 60 ml of diethyl ether and 65 ml of acetonitrile were admixed at 0° C. with 1.21 g (27.7 mmol) of sodium hydride (55% strength), divided into 3 portions, and then stirred for 90 minutes at 15° C. The mixture was admixed with dilute sodium chloride solution and extracted (3×) with ethyl acetate. The combined organic phases were dried (Na₂SO₄), filtered and concentrated by evaporation. The resulting residue was purified chromatographically (hexane/ethyl acetate 95:5). This gave 1.60 g (4.4 mmol; yield: 19%) of the product.

Compound 1.7

[4-((1R,2R)-2-Benzyloxy-1-methylpropoxy)-5-trifluoromethylpyrimidin-2-yl](4-cyclopropane-sulphonylphenyl)amine

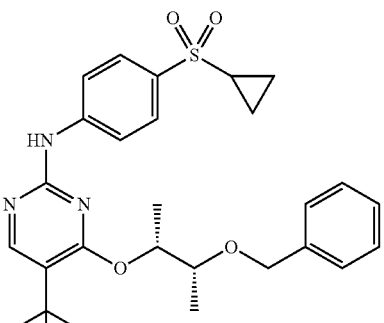

700 mg (1.94 mmol) of 4-((1R,2R)-2-benzyloxy-1-methylpropoxy)-2-chloro-5-trifluoromethylpyrimidine and 460 mg (2.33 mmol) of 4-cyclopropanesulphonyl-phenylamine in 9.5 ml of acetonitrile were admixed with 0.49 ml of a 4N solution of hydrogen chloride in dioxane and stirred for 5.5 hours at 80° C. After cooling, the mixture was diluted with ethyl acetate and washed with saturated sodium hydrogen carbonate solution and saturated sodium chloride solution, dried (Na₂SO₄), filtered and concentrated by evaporation. The resulting residue was purified chromatographically (DCM/ethanol 95:5). This gave 649 mg (1.24 mmol, yield: 64%) of the product.

¹H NMR (400 MHz, DMSO): δ=10.55 (s, 1H), 8.58 (s, 1H), 7.96 (m, 2H), 7.79 (m, 2H), 7.22 (m, 5H), 5.48 (m, 1H), 4.57 (d, 1H), 4.46 (d, 1H), 3.73 (m, 1H), 2.71 (m, 1H), 1.31 (d, 3H), 1.15 (d, 3H), 1.05 (m, 2H), 0.96 (m, 2H).

MS: 522 (ESI+)

b) Preparation of the End Product

A solution of 541 mg (1.04 mmol) of [4-((1R,2R)-2-benzyloxy-1-methylpropoxy)-5-trifluoromethylpyrimidin-2-yl](4-cyclopropanesulphonylphenyl)amine in 110 ml of ethanol was admixed with 541 mg of palladium on carbon (10%) and hydrogenated under atmospheric pressure at room temperature for one hour. The mixture was filtered and concentrated by evaporation. The resulting residue was purified chromatographically (DCM/EtOH 98:2). This gave 175 mg (0.41 mmol; yield: 39%) of the product.

¹H NMR (400 MHz, DMSO): δ=10.54 (s, 1H), 8.56 (s, 1H), 7.95 (m, 2H), 7.79 (m, 2H), 5.28 (m, 1H), 4.86 (d, 1H), 3.83 (m, 1H), 2.76 (m, 1H), 1.26 (d, 3H), 1.01 (m, 7H).

MS: 432 (ESI+).

EXAMPLE 2

(2R,3R)-3-[2-(4-Methanesulphonylphenylamino)-5-trifluoromethylpyrimidin-4-yloxy]butan-2-ol

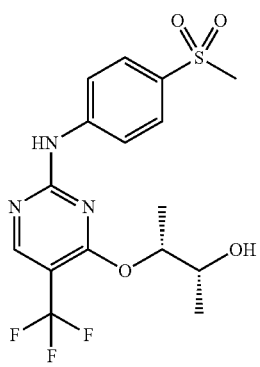 [SMILES: C[C@@H](O)[C@@H](C)Oc1nc(Nc2ccc(S(C)(=O)=O)cc2)ncc1C(F)(F)F]

2a) Preparation of the Intermediates

Compound 2.1

[4-((1R,2R)-2-Benzyloxy-1-methylpropoxy)-5-trifluoro-methylpyrimidin-2-yl]-(4-methanesulphonylphenyl)amine

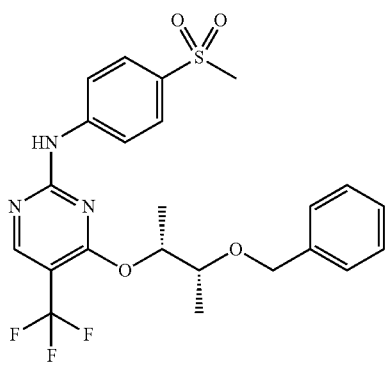 [SMILES: C[C@@H](OCc1ccccc1)[C@@H](C)Oc1nc(Nc2ccc(S(C)(=O)=O)cc2)ncc1C(F)(F)F]

810 mg (2.25 mmol) of 4-((1R,2R)-2-benzyloxy-1-methylpropoxy)-2-chloro-5-trifluoromethylpyrimidine and 559 mg (2.69 mmol) of 4-methanesulphonylphenylamine hydrochloride (Acros) in 11 ml of acetonitrile were stirred for 16 hours at 80° C. After cooling, the mixture was diluted with ethyl acetate and washed with saturated sodium hydrogen carbonate solution and saturated NaCl solution, dried (Na$_2$SO$_4$), filtered and concentrated by evaporation. The resulting residue was purified chromatographically (hexane/ethyl acetate 1:1). This gave 770 mg (1.55 mmol; yield: 69%) of the product.

$^1$H NMR (400 MHz, DMSO): δ=10.55 (s, 1H), 8.58 (s, 1H), 7.95 (m, 2H), 7.83 (m, 2H), 7.22 (m, 5H), 5.48 (m, 1H), 4.57 (d, 1H), 4.46 (d, 1H), 3.72 (m, 1H), 3.12 (s, 3H), 1.31 (d, 3H), 1.15 (d, 3H).

MS: 496 (ESI+)

b) Preparation of the End Product

A solution of 750 mg (1.51 mmol) of [4-((1R,2R)-2-benzyloxy-1-methylpropoxy)-5-trifluoromethylpyrimidin-2-yl]-(4-methanesulphonylphenyl)amine in 20 ml of ethanol was admixed with 152 mg of palladium on carbon (10%) and hydrogenated under atmospheric pressure at room temperature for 30 minutes. The mixture was admixed again with 152 mg of palladium on carbon (10%) and hydrogenated for 1.5 hours. A further 152 mg of palladium on carbon (10%) were added and the mixture was hydrogenated for 1 hour. Finally, 152 mg of palladium on carbon (10%) were again added and the mixture was hydrogenated for 15 minutes. The mixture was filtered and concentrated by evaporation. The resulting residue was purified chromatographically (DCM/EtOH 95:5). This gave 512 mg (1.26 mmol; yield: 83%) of the product.

$^1$H NMR (400 MHz, DMSO): δ=10.55 (s, 1H), 8.57 (s, 1H), 7.96 (m, 2H), 7.83 (m, 2H), 5.27 (m, 1H), 4.86 (d, 1H), 3.82 (m, 1H), 3.14 (s, 3H), 1.25 (d, 3H), 1.07 (d, 3H).

MS: 405 (EI+).

EXAMPLE 3

(R)-3-[2-(4-Methanesulphonylphenylamino)-5-trifluoromethylpyrimidin-4-yloxy]-2-methylbutan-2-ol

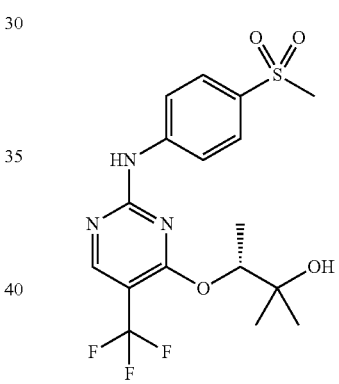

3a) Preparation of the Intermediates

Compound 3.1

(R)-2-Methylbutane-2,3-diol

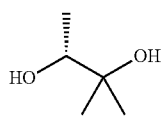

A solution of 10.0 g (96.1 mmol) of methyl(R)-(+)-lactate in 20 ml of THF was slowly added dropwise to 160 ml (480.0 mmol) of an ice-cooled 3N solution of methylmagnesium chloride in THF. The mixture was firstly heated slowly to room temperature and then refluxed for 30 minutes. After cooling, the mixture was added to a saturated ammonium chloride solution and extracted (3×) with ethyl acetate. The combined organic phases were filtered through a Whatman filter and concentrated by evaporation. This gave 4.5 g (43.1 mmol) of the crude product, which was used without further purification.

$^1$H NMR (400 MHz, DMSO): δ=4.21 (d, 1H), 3.93 (s, 1H), 3.29 (m, 1H), 0.97 (m, 9H).

Compound 3.2

(R)-3-(2-Chloro-5-iodopyrimidin-4-yloxy)-2-methylbutan-2-ol

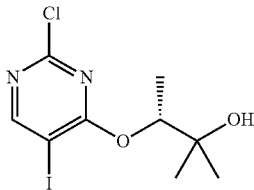

A solution of 4.40 g (42.3 mmol) of (R)-2-methylbutane-2,3-diol in 83 ml of diethyl ether was admixed with stirring at 0° C. in portions with 1.84 g (42.3 mmol) of sodium hydride (55%) and stirred for 10 minutes. The mixture was stirred for a further 3 minutes at room temperature and then added to an ice-cooled solution of 9.68 g (35.2 mmol) of 2,4-dichloro-5-iodopyrimidine in 97 ml of acetonitrile. The mixture was stirred for 4 hours at 40° C. and, after cooling, admixed with ice and saturated NaCl solution. The mixture was extracted (3×) with ethyl acetate. The combined organic phases were dried (Na$_2$SO$_4$), filtered and concentrated by evaporation. The resulting residue was purified chromatographically (hexane/ethyl acetate 4:1). This gave 4.96 g (14.5 mmol; yield: 41%) of the product.

$^1$H NMR (400 MHz, DMSO): δ=8.73 (s, 1H), 4.96 (q, 1H), 4.62 (s, 1H), 1.21 (d, 3H), 1.13 (s, 6H).

ES: 343 (Cl$^+$).

Compound 3.3

2-Chloro-4-[(R)-1,2-dimethyl-2-(tetrahydropyran-2-yl-oxy)propoxy]-5-iodopyrimidine

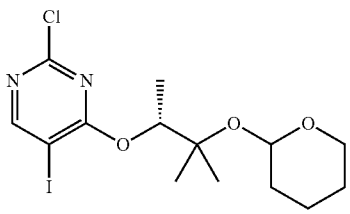 [SMILES: C[C@@H](Oc1nc(Cl)ncc1I)C(C)(C)OC1CCCCO1]

A solution of 4.96 g (14.5 mmol) of (R)-3-(2-chloro-5-iodopyrimidin-4-yloxy)-2-methylbutan-2-ol in 30 ml of DCM was admixed with 2.64 ml (29.0 mmol) of dihydropyrane and 0.36 g (1.5 mmol) of pyridinium tosylate and stirred for 22 hours at room temperature. The mixture was diluted with DCM and washed with saturated sodium hydrogen carbonate solution. The organic phase was dried (Na$_2$SO$_4$), filtered and concentrated by evaporation. The resulting residue was purified chromatographically (hexane/ethyl acetate 4:1). This gave 5.50 g (12.9 mmol; yield: 89%) of the diastereomer mixture.

$^1$H NMR (400 MHz, DMSO): δ=8.75 (s, 1H), 8.74 (s, 1H), 5.15 (m, 2H), 4.91 (m, 2H), 3.70 (m, 2H), 3.30 (m, 2H), 1.31 (m, 30H).

Compound 3.4

2-Chloro-4-[(R)-1,2-dimethyl-2-(tetrahydropyran-2-yl-oxy)propoxy]-5-trifluoromethylpyrimidine

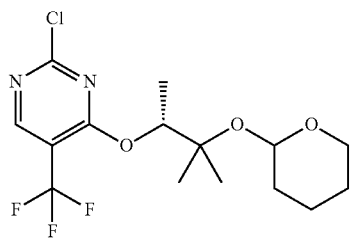 [SMILES: C[C@@H](Oc1nc(Cl)ncc1C(F)(F)F)C(C)(C)OC1CCCCO1]

A solution of 1.00 g (2.34 mmol) of 2-chloro-4-[(R)-1,2-dimethyl-2-(tetrahydropyran-2-yloxy)propoxy]-5-iodopyrimidine in 3.3 ml of NMP and 3.3 ml of THF was admixed at room temperature with 1.61 g (8.44 mmol) of copper(I) iodide, 0.41 g (7.03 mmol) of potassium fluoride and 1.04 ml (7.03 mmol) of (trifluoromethyl)trimethylsilane. The mixture was stirred for 2 hours at 90° C. After cooling, the mixture was added to dilute sodium chloride solution and extracted (3×) with ethyl acetate. The combined organic phases were dried (Na$_2$SO$_4$), filtered and concentrated by evaporation. The resulting residue was purified chromatographically (hexane/ethyl acetate 4:1). This gave 0.53 g (1.43 mmol; yield: 61%) of the product.

$^1$H NMR (400 MHz, DMSO): δ=8.84 (s, 1H), 5.32 (m, 1H), 4.85 (m, 1H), 3.68 (m, 1H), 3.30 (m, 1H), 1.31 (m, 15H)

b) Preparation of the End Product 100 mg (0.27 mmol) of 2-chloro-4-[(R)-1,2-dimethyl-2-(tetrahydropyran-2-yloxy)propoxy]-5-trifluoromethylpyrimidine and 37 mg (0.22 mmol) of 4-methanesulphonylphenylamine in 2.5 ml of ethanol were stirred for 150 minutes at 70° C. The mixture was evaporated to dryness, taken up with 3.1 ml of ethanol and admixed with 12 mg (0.05 mmol) of pyridinium tosylate. The mixture was stirred for 4 hours at 45° C. After cooling, the mixture was admixed with dilute sodium hydrogen carbonate solution and extracted (3×) with ethyl acetate. The combined organic phases were dried (Na$_2$SO$_4$), filtered and concentrated by evaporation. The resulting residue was purified chromatographically (DCM/ethanol 95:5). This gave 42 mg (0.10 mmol; yield: 45%) of the product.

$^1$H NMR (400 MHz, DMSO): δ=10.55 (s, 1H), 8.57 (s, 1H), 7.96 (m, 2H), 7.84 (m, 2H), 5.14 (q, 1H), 4.66 (s, 1H), 3.14 (s, 3H), 1.28 (d, 3H), 1.12 (s, 6H).

MS: 419 (EI+)

EXAMPLE 4

(R)-3-[2-(4-Cyclopropanesulphonylphenylamino)-5-tri-fluoromethylpyrimidin-4-yloxy]-2-methylbutan-2-ol

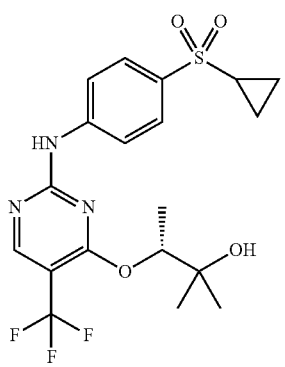 [SMILES: C[C@@H](Oc1nc(Nc2ccc(S(=O)(=O)C3CC3)cc2)ncc1C(F)(F)F)C(C)(C)O]

Preparation of the End Product 200 mg (0.54 mmol) of 2-chloro-4-[(R)-1,2-dimethyl-2-(tetrahydropyran-2-yloxy)propoxy]-5-trifluoromethylpyrimidine and 64 mg (0.33 mmol) of 4-cyclopropanesulphonylphenylamine in 5.0 ml of ethanol were stirred for 210 minute at 70° C. The mixture was admixed again with 100 mg (0.27 mmol) of 2-chloro-4-[(R)-1,2-dimethyl-2-(tetrahydropyran-2-yloxy)propoxy]-5-trifluoromethylpyrimidine and stirred for a further 210 minutes at 70° C. The mixture was evaporated to dryness and the resulting residue was purified by means of HPLC. This gave 91 mg (0.20 mmol; yield: 61%) of the product.

| Column: | XBridge C18 5μ 100 × 30 mm | | |
|---|---|---|---|
| Eluent A: | H$_2$O/0.2% NH$_3$ | | |
| Eluent B: | Acetonitrile | | |
| Gradient: | 0 min | 50% A | 50% B |
| | 1.00 min | 50% A | 50% B |
| | 7.50 min | 20% A | 80% B |
| | 7.52 min | 1% A | 99% B |
| | 10.00 min | 1% A | 99% B |
| Flow: | 50.0 ml/min | | |
| Detector: | DAD scan range 210-400 nm | | |
| | MS ESI+, ESI−, scan range 160-1000 m/z | | |
| Temperature: | Room temperature | | |
| Retention time: | 4.6-5.5 min | | |

$^1$H NMR (400 MHz, DMSO): 10.56 (br, 1H), 8.57 (s, 1H), 7.96 (m, 2H), 7.80 (m, 2H), 5.14 (q, 1H), 4.66 (s, 1H), 2.77 (m, 1H), 1.28 (d, 3H), 1.12 (m, 6H), 1.07 (m, 2H), 0.97 (m, 2H).

MS: 445 (EI+)

EXAMPLE 5

(2R,3R)-3-[2-(4-Benzenesulphonylphenylamino)-5-tri-fluoromethylpyrimidin-4-yloxy]butan-2-ol

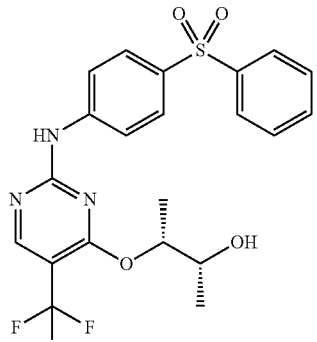

5a) Preparation of the Intermediates

Compound 5.1

(4-Benzenesulphonylphenyl)[4-((1R,2R)-2-benzyloxy-1-methylpropoxy)-5-trifluoromethylpyrimidin-2-yl]amine

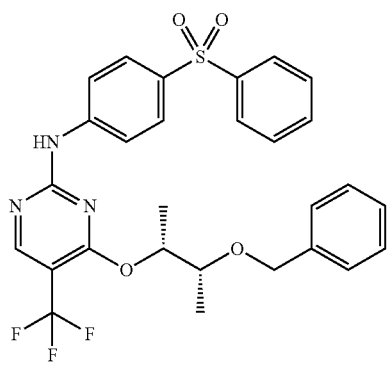 [SMILES: C[C@@H](OCc1ccccc1)[C@@H](C)Oc1nc(Nc2ccc(S(=O)(=O)c3ccccc3)cc2)ncc1C(F)(F)F]

110 mg (0.30 mmol) of 4-((1R,2R)-benzyloxy-1-methylpropoxy)-2-chloro-5-trifluoromethylpyrimidine and 85 mg (0.37 mmol) of 4-benzenesulphonylphenylamine in 1.5 ml of acetonitrile were admixed with 0.08 ml of a 4N solution of hydrogen chloride in dioxane and stirred for 5 hours at 80° C. The mixture was concentrated in a rotary evaporator and the resulting residue was purified by means of HPLC. This gave 121 mg (0.22 mmol, yield: 71%) of the product.

| System: | Waters Autopurification | | |
|---|---|---|---|
| Column: | XBridge C18 5μ 100 × 30 mm | | |
| Eluent A: | H$_2$O/0.1% HCOOH | | |
| Eluent B: | Acetonitrile | | |
| Gradient: | 0 min | 99% A | 1% B |
| | 1.00 min | 99% A | 1% B |
| | 7.50 min | 1% A | 99% B |
| | 10.00 min | 1% A | 99% B |
| Flow: | 50.0 ml/min | | |
| Detector: | DAD scan range 210-400 nm | | |
| | MS ESI+, ESI−, scan range 160-1000 m/z | | |
| Temperature: | Room temperature | | |

$^1$H NMR (400 MHz, DMSO): δ=10.56 (s. 1H), 8.56 (s, 1H), 7.89 (m, 6H), 7.58 (m, 3H), 7.22 (m, 5H), 5.44 (m, 1H), 4.55 (d, 1H), 4.44 (d, 1H), 3.71 (m, 1H), 1.29 (d, 3H), 1.14 (d, 3H).

b) Preparation of the End Product

A solution of 116 mg (0.21 mmol) of (4-benzenesulphonylphenyl)[4-((1R,2R)-2-benzyloxy-1-methylpropoxy)-5-trifluoromethylpyrimidin-2-yl]amine in 5 ml of ethanol was hydrogenated for 2.5 hours at room temperature under a hydrogen atmosphere. Here, the mixture was admixed 6× with in each case 50 mg portions of palladium on carbon (10%). The mixture was filtered and concentrated by evaporation. This gave 63 mg (0.13 mmol; yield: 65%) of the product.

¹H NMR (400 MHz, DMSO): δ=10.55 (s, 1H), 8.55 (s, 1H), 7.89 (m, 6H), 7.59 (m, 3H), 5.25 (m, 1H), 4.86 (d, 1H), 3.80 (m, 1H), 1.24 (d, 3H), 1.06 (d, 3H).

MS: 468 (ESI+)

EXAMPLE 6

(2R,3R)-3-{2-[4-(Difluoromethanesulphonyl)phenylamino]-5-trifluoromethylpyrimidin-4-yloxy}butan-2-ol

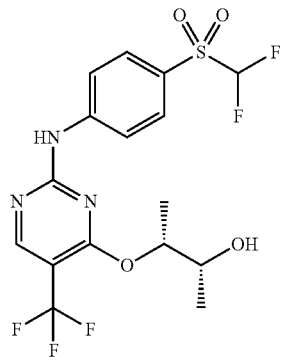 [SMILES: C[C@@H](O)[C@@H](C)Oc1nc(Nc2ccc(S(=O)(=O)C(F)F)cc2)ncc1C(F)(F)F]

6a) Preparation of the Intermediates

Compound 6.1

[4-((1R,2R)-2-Benzyloxy-1-methylpropoxy)-5-trifluoro-methylpyrimidin-2-yl][4-(difluoromethanesulphonyl)phenyl]amine

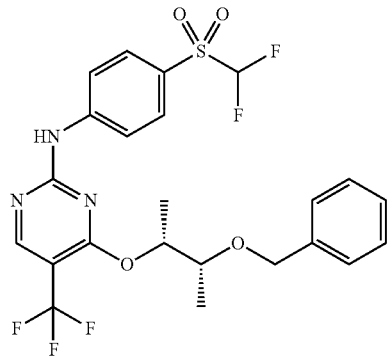 [SMILES: C[C@@H](OCc1ccccc1)[C@@H](C)Oc1nc(Nc2ccc(S(=O)(=O)C(F)F)cc2)ncc1C(F)(F)F]

100 mg (0.28 mmol) of 4-((1R,2R)-2-benzyloxy-1-methyl-propoxy)-2-chloro-5-trifluoromethylpyrimidine and 69 mg (0.33 mmol) of 4-(difluoromethanesulphonyl)phenylamine in 1.4 ml of acetonitrile were admixed with 0.07 ml of a 4N solution of hydrogen chloride in dioxane and stirred for 3 hours at 80° C. The mixture was concentrated in a rotary evaporator and the resulting residue was purified by means of HPLC. This gave 104 mg (0.20 mmol; yield: 71%) of the product.

| System: | Waters Autopurification | | |
|---|---|---|---|
| Column: | XBridge C18 5µ 100 × 30 mm | | |
| Eluent A: | H₂O/0.1% HCOOH | | |
| Eluent B: | Acetonitrile | | |
| Gradient: | 0 min | 99% A | 1% B |
| | 1.00 min | 99% A | 1% B |
| | 7.50 min | 1% A | 99% B |
| | 10.00 min | 1% A | 99% B |
| Flow: | 50.0 ml/min | | |
| Detector: | DAD scan range 210-400 nm | | |
| | MS ESI+, ESI−, scan range | | |
| | 160-1000 m/z | | |
| Temperature: | Room temperature | | |

¹H NMR (400 MHz, DMSO): δ=10.77 (s, 1H), 8.62 (s, 1H), 8.07 (m, 2H), 7.88 (m, 2H), 7.22 (m, 6H), 5.47 (m, 1H), 4.57 (d, 1H), 4.45 (d, 1H), 3.72 (m, 1H), 1.31 (d, 3H), 1.15 (d, 3H).

b) Preparation of the End Product

A solution of 100 mg (0.19 mmol) of [4-((1R,2R)-2-benzyloxy-1-methylpropoxy)-5-trifluoromethylpyrimidin-2-yl][4-(difluoromethanesulphonyl)phenyl]amine in 5 ml of ethanol was hydrogenated for 1.5 hours at room temperature under a hydrogen atmosphere. Here, the mixture was admixed 3× with in each case 100 mg portions of palladium on carbon (10%). The mixture was filtered and concentrated by evaporation. This gave 45 mg (0.10 mmol; yield: 54%) of the product.

¹H NMR (400 MHz, DMSO): δ=10.77 (s, 1H), 8.61 (s, 1H), 8.08 (m, 2H), 7.88 (m, 2H), 7.20 (tr, 1H), 5.29 (m, 1H), 4.88 (d, 1H), 3.84 (m, 1H), 1.26 (d, 3H), 1.07 (d, 3H)

MS: 442 (ESI+)

EXAMPLE 7

(2R,3R)-3-[2-(4-Cyclopentanesulphonylphenylamino)-5-triluoromethylpyrimidin-4-yloxy]butan-2-ol

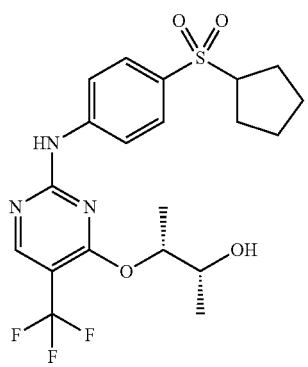 [SMILES: C[C@@H](O)[C@@H](C)Oc1nc(Nc2ccc(S(=O)(=O)C3CCCC3)cc2)ncc1C(F)(F)F]

7a) Preparation of the Intermediates

Compound 7.1

[4]-((1R,2R)-2-Benzyloxy-1-methylpropoxy)-5-trifluoromethylpyrimidin-2-yl]-(4-cyclopentanesulphonylphenyl)amine

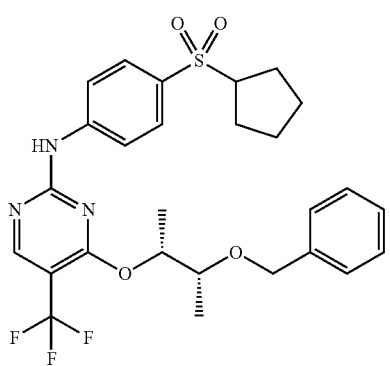 [SMILES: C[C@@H](OCc1ccccc1)[C@@H](C)Oc1nc(Nc2ccc(S(=O)(=O)C3CCCC3)cc2)ncc1C(F)(F)F]

100 mg (0.28 mmol) of 4-((1R,2R)-2-benzyloxy-1-methylpropoxy)-2-chloro-5-trifluoromethylpyrimidine and 75 mg (0.33 mmol) of 4-cyclopentanesulphonylphenylamine in 1.4 ml of acetonitrile were admixed with 0.07 ml of a 4N solution of hydrogen chloride in dioxane and stirred for 5 hours at 80° C. The mixture was concentrated in a rotary evaporator and the resulting residue was purified by means of HPLC. This gave 118 mg (0.21 mmol, yield: 77%) of the product.

| System: | Waters Autopurification | | |
|---|---|---|---|
| Column: | XBridge C18 5μ 100 × 30 mm | | |
| Eluent A: | H₂O/0.1% HCOOH | | |
| Eluent B: | Acetonitrile | | |
| Gradient: | 0 min | 99% A | 1% B |
| | 1.00 min | 99% A | 1% B |
| | 7.50 min | 1% A | 99% B |
| | 10.00 min | 1% A | 99% B |
| Flow: | 50.0 ml/min | | |
| Detector: | DAD scan range 210-400 nm | | |
| | MS ESI+, ESI−, scan range 160-1000 m/z | | |
| Temperature: | Room temperature | | |

$^1$H NMR (400 MHz, DMSO): δ=10.57 (s, 1H), 8.58 (s, 1H), 7.96 (m, 2H), 7.77 (m, 2H), 7.22 (m, 5H), 5.48 (m, 1H), 4.56 (d, 1H), 4.46 (d, 1H), 3.72 (m, 1H), 3.63 (m, 1H), 1.76 (m, 4H), 1.51 (m, 4H), 1.30 (d, 3H), 1.14 (d, 3H).

b) Preparation of the End Product

A solution of 112 mg (0.20 mmol) of [4-((1R,2R)-2-benzyloxy-1-methylpropoxy)-5-trifluoromethylpyrimidin-2-yl](4-cyclopentanesulphonylphenyl)amine in 5 ml of ethanol was hydrogenated for 2.5 hours at room temperature under a hydrogen atmosphere. Here, the mixture was admixed 5× with in each case 100 mg portions of palladium on carbon (10%). The mixture was filtered and concentrated by evaporation. This gave 75 mg (0.16 mmol; yield: 80%) of the product.

$^1$H NMR (400 MHz, DMSO): δ=10.58 (s, 1H), 8.57 (s, 1H), 7.97 (m, 2H), 7.78 (m, 2H), 5.28 (m, 1H), 4.88 (d, 1H), 3.83 (m, 1H), 3.68 (m, 1H), 1.76 (m, 4H), 1.55 (m, 4H), 1.25 (d, 3H), 1.07 (d, 3H).

MS: 460 (ESI+)

EXAMPLE 8

(R)-2-Methyl-3-{2-[4-(prop-2-ene-1-sulphonyl)phenylamino]-5-trifluoromethylpyrimidin-4-yloxy}butan-2-ol

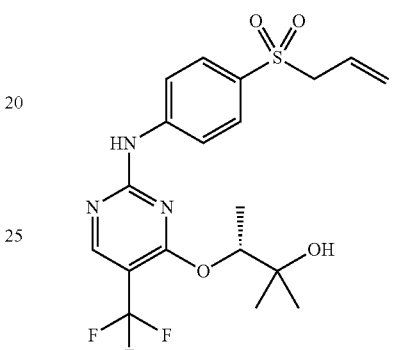

Preparation of the End Product 104 mg (0.28 mmol) of 2-chloro-4-[(R)-1,2-dimethyl-2-(tetrahydropyran-2-yloxy)propoxy]-5-trifluoromethylpyrimidine and 33 mg (0.17 mmol) of 4-(prop-2-ene-1-sulphonyl)phenylamine in 2.6 ml of ethanol were stirred for 10 hours at 70° C. The mixture was evaporated to dryness and the residue was purified by means of HPLC. This gave 12 mg (0.03 mmol; yield: 10%) of the product.

| System: | Waters Autopurification | | |
|---|---|---|---|
| Column: | XBridge C18 5μ 100 × 30 mm | | |
| Eluent A: | H₂O/0.1% HCOOH | | |
| Eluent B: | Acetonitrile | | |
| Gradient: | 0 min | 99% A | 1% B |
| | 1.00 min | 99% A | 1% B |
| | 7.50 min | 1% A | 99% B |
| | 10.00 min | 1% A | 99% B |
| Flow: | 50.0 ml/min | | |
| Detector: | DAD scan range 210-400 nm | | |
| | MS ESI+, ESI−, scan range 160-1000 m/z | | |
| Temperature: | Room temperature | | |

$^1$H NMR (400 MHz, DMSO): δ=10.57 (s, 1H), 8.58 (s, 1H), 7.95 (m, 2H), 7.76 (m, 2H), 5.64 (m, 1H), 5.25 (m, 1H), 5.17 (m, 2H), 4.67 (s, 1H), 4.04 (d, 2H), 1.28 (d, 3H), 1.12 (s, 6H).

EXAMPLE 9

(2R,3R)-3-{2-[4-(Propane-2-sulphonyl)phenylamino]-5-trifluoromethylpyrimidin-4-yloxy}butan-2-ol

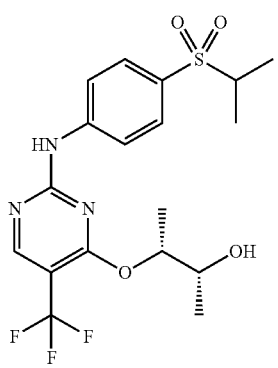 [SMILES: CC(C)S(=O)(=O)c1ccc(Nc2ncc(C(F)(F)F)c(O[C@H](C)[C@@H](C)O)n2)cc1]

9a) Preparation of the Intermediates

Compound 9.1

[4-((1R,2R)-2-Benzyloxy-1-methylpropoxy)-5-trifluoromethylpyrimidin-2-yl][4-(propane-2-sulphonyl)phenyl]amine

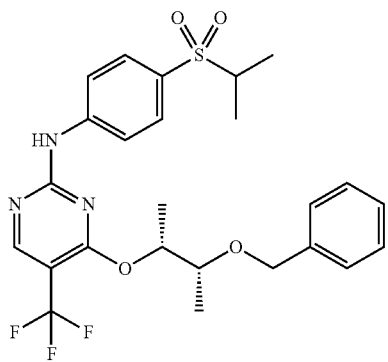 [SMILES: CC(C)S(=O)(=O)c1ccc(Nc2ncc(C(F)(F)F)c(O[C@H](C)[C@@H](C)OCc3ccccc3)n2)cc1]

103 mg (0.29 mmol) of 4-((1R,2R)-2-benzyloxy-1-methyl-propoxy)-2-chloro-5-trifluoromethylpyrimidine and 68 mg (0.34 mmol) of 4-(propane-2-sulphonyl)phenylamine in 1.4 ml of acetonitrile were admixed with 0.07 ml of a 4N solution of hydrogen chloride in dioxane and stirred for 5 hours at 80° C. The mixture was concentrated in a rotary evaporator and the resulting residue was purified by means of HPLC. This gave 123 mg (0.22 mmol, yield: 82%) of the product.

| System: | Waters Autopurification | | |
|---|---|---|---|
| Column: | XBridge C18 5μ 100 × 30 mm | | |
| Eluent A: | H₂O/0.1% HCOOH | | |
| Eluent B: | Acetonitrile | | |
| Gradient: | 0 min | 99% A | 1% B |
| | 1.00 min | 99% A | 1% B |
| | 7.50 min | 1% A | 99% B |
| | 10.00 min | 1% A | 99% B |
| Flow: | 50.0 ml/min | | |
| Detector: | DAD scan range 210-400 nm | | |
| | MS ESI+, ESI−, scan range 160-1000 m/z | | |
| Temperature: | Room temperature | | |

¹H NMR (400 MHz, DMSO): δ=10.59 (S, 1H), 8.58 (s, 1H), 7.96 (m, 2H), 7.75 (m, 2H), 7.22 (m, 5H), 5.48 (m, 1H), 4.55 (d, 1H), 4.45 (d, 1H), 3.72 (m, 1H), 3.27 (m, 1H), 1.30 (d, 3H), 1.14 (d, 3H), 1.09 (d, 6H).

b) Preparation of the End Product

A solution of 118 mg (0.23 mmol) of [4-((1R,2R)-2-benzyloxy-1-methylpropoxy)-5-trifluoromethylpyrimidin-2-yl][4-(propane-2-sulphonyl)phenyl]amine in 5 ml of ethanol was hydrogenated for 1.5 hours at room temperature under a hydrogen atmosphere. Here, the mixture was admixed 4× with in each case 50 mg portions of palladium on carbon (10%). The mixture was filtered and concentrated by evaporation. This gave 43 mg (0.10 mmol; yield: 44%) of the product.

¹H NMR (400 MHz, DMSO): δ=10.58 (s, 1H), 8.57 (s, 1H), 7.98 (m, 2H), 7.76 (m, 2H), 5.27 (m, 1H), 4.87 (d, 1H), 3.81 (m, 1H), 3.31 (m, 1H), 1.25 (d, 3H), 1.11 (d, 6H), 1.06 (d, 3H).

MS: 434 (ESI+)

EXAMPLE 10

(R)-2-Methyl-3-{2-[4-(prop-2-yne-1-sulphonyl)phenylamino]-5-trifluoromethylpyrimidin-4-yloxy}butan-2-ol

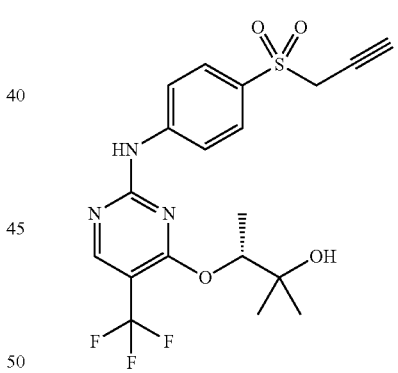

Preparation of the End Product 150 mg (0.41 mmol) of 2-chloro-4-[(R)-1,2-dimethyl-2-(tetrahydropyran-2-yloxy)propoxy]-5-trifluoromethylpyrimidine and 47 mg (0.24 mmol) of 4-(prop-2-yne-1-sulphonyl)phenylamine in 3.6 ml of ethanol were stirred for 200 minutes at 70° C. The mixture was evaporated to dryness. This gave ca. 147 mg of the crude product, of which 60 mg were purified by means of HPLC. This gave 31 mg (0.07 mmol) of the product.

| System: | Waters Autopurification |
|---|---|
| Column: | XBridge C18 5μ 100 × 30 mm |
| Eluent A: | H₂O/0.1% HCOOH |

-continued

| | | | |
|---|---|---|---|
| Eluent B: | Acetonitrile | | |
| Gradient: | 0 min | 99% A | 1% B |
| | 1.00 min | 99% A | 1% B |
| | 7.50 min | 1% A | 99% B |
| | 10.00 min | 1% A | 99% B |
| Flow: | 50.0 ml/min | | |
| Detector: | DAD scan range 210-400 nm | | |
| | MS ESI+, ESI−, scan range | | |
| | 160-1000 m/z | | |
| Temperature: | Room temperature | | |

$^1$H NMR (400 MHz, DMSO): δ=10.60 (s, 1H), 8.58 (s, 1H), 7.98 (m, 2H), 7.83 (m, 2H), 5.14 (q, 1H), 4.67 (s, 1H), 4.45 (d, 2H), 3.38 (tr, 1H), 1.28 (d, 3H), 1.10 (m, 6H).
MS: 444 (ESI+)

EXAMPLE 11

(2R,3R)-3-{2-[4-(2-Hydroxyethanesulphonyl)phenylamino]-5-trifluoromethylpyrimidin-4-yloxy}butan-2-ol

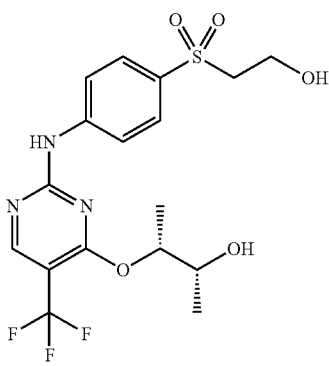 [SMILES: C[C@@H](O)[C@@H](C)Oc1nc(Nc2ccc(S(=O)(=O)CCO)cc2)ncc1C(F)(F)F]

11a) Preparation of the Intermediates

Compound 11.1

2-{4-[4-((1R,2R)-2-Benzyloxy-1-methylpropoxy)-5-trifluoromethylpyrimidin-2-ylamino]benzenesulphonyl}ethanol

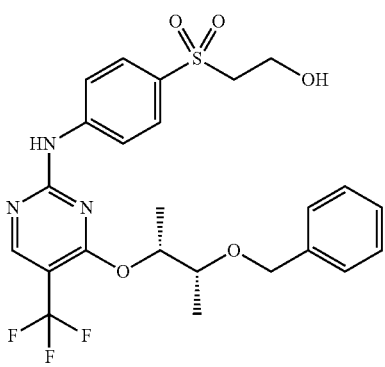 [SMILES: C[C@@H](OCc1ccccc1)[C@@H](C)Oc1nc(Nc2ccc(S(=O)(=O)CCO)cc2)ncc1C(F)(F)F]

102 mg (0.28 mmol) of 4-((1R,2R)-2-benzyloxy-1-methyl-propoxy)-2-chloro-5-trifluoromethylpyrimidine and 68 mg (0.34 mmol) of 2-(4-aminobenzenesulphonyl)ethanol in 1.4 ml of acetonitrile were admixed with 0.07 ml of a 4N solution of hydrogen chloride in dioxane and stirred for 4 hours at 80° C. The mixture was concentrated in a rotary evaporator and the resulting residue was purified by means of HPLC. This gave 72 mg (0.14 mmol, yield: 48%) of the product.

| | | | |
|---|---|---|---|
| System: | Waters Autopurification | | |
| Column: | XBridge C18 5μ 100 × 30 mm | | |
| Eluent A: | H$_2$O/0.1% HCOOH | | |
| Eluent B: | Acetonitrile | | |
| Gradient: | 0 min | 99% A | 1% B |
| | 1.00 min | 99% A | 1% B |
| | 7.50 min | 1% A | 99% B |
| | 10.00 min | 1% A | 99% B |
| Flow: | 50.0 ml/min | | |
| Detector: | DAD scan range 210-400 nm | | |
| | MS ESI+, ESI−, scan range | | |
| | 160-1000 m/z | | |
| Temperature: | Room temperature | | |

$^1$H NMR (400 MHz, DMSO): δ=10.56 (s, 1H), 8.58 (s, 1H), 7.94 (m, 2H), 7.79 (m, 2H), 7.22 (m, 5H), 5.46 (m, 1H), 4.83 (tr, 1H), 4.56 (d, 1H), 4.46 (d, 1H), 3.72 (m, 1H), 3.62 (m, 2H), 3.35 (m, 2H), 1.30 (d, 3H), 1.15 (d, 3H).

b) Preparation of the End Product

A solution of 68 mg (0.13 mmol) of (2-{4-[4-((1R,2R)-2-benzyloxy-1-methylpropoxy)-5-trifluoromethylpyrimidin-2-ylamino]benzenesulphonyl}ethanol in 5 ml of ethanol was hydrogenated for one hour at room temperature under a hydrogen atmosphere. Here, the mixture was admixed with in each case 68 mg of palladium on carbon (10%). The mixture was filtered and concentrated by evaporation. This gave 28 mg (0.06 mmol; yield: 50%) of the product.

$^1$H NMR (400 MHz, DMSO): δ=10.55 (s, 1H), 8.57 (s, 1H), 7.95 (m, 2H), 7.79 (m, 2H), 5.27 (m, 1H), 4.87 (d, 1H), 4.84 (tr, 1H), 3.82 (m, 1H), 3.63 (m, 2H), 3.36 (m, 2H), 1.25 (d, 3H), 1.07 (d, 3H).
MS: 436 (ESI+)

EXAMPLE 12

(4-Methanesulphonylphenyl) [4-((R)-2-methoxy-1-methyl-ethoxy)-5-trifluoromethylpyrimidin-2-yl]amine

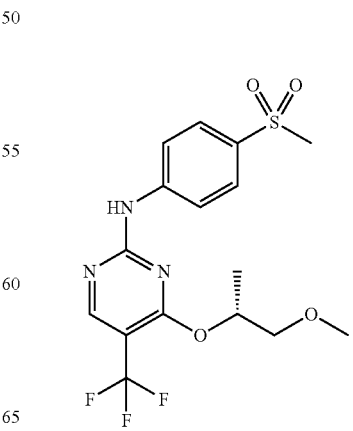

a) Preparation of the Intermediates

Compound 12.1

2-Chloro-4-((R)-2-methoxy-1-methylethoxy)-5-trifluoro-methylpyrimidine

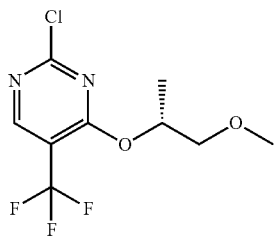 [SMILES: COC[C@@H](C)Oc1nc(Cl)ncc1C(F)(F)F]

A solution of 2.00 g (9.2 mmol) of 2,4-dichloro-5-trifluoromethylpyrimidine and 1.08 g (12.0 mmol) of (R)-1-methoxypropan-2-ol in 24.4 ml of diethyl ether and 24.4 ml of acetonitrile were admixed at 0° C. with stirring in portions with 0.48 g of sodium hydride (55%). The mixture was slowly warmed to room temperature in an ice bath. After 3.5 hours, the mixture was admixed with ice and dilute sodium chloride solution. Extraction was carried out with ethyl acetate (2×). The combined organic phases were dried ($Na_2SO_4$), filtered and concentrated by evaporation. The resulting residue was purified chromatographically (hexane/ethyl acetate 7:3). This gave 0.59 g (2.2 mmol; yield: 24%) of the product.

$^1$H NMR (400 MHz, DMSO): δ=8.83 (s, 1H), 5.50 (m, 1H), 3.50 (d, 2H), 3.24 (s, 3H), 1.26 (d, 3H).

b) Preparation of the End Product 100 mg (0.37 mmol) of 2-chloro-4-((R)-2-methoxy-1-methylethoxy)-5-trifluoromethylpyrimidine and 63 mg (0.37 mmol) of 4-methanesulphonylphenylamine in 2.6 ml of acetonitrile were admixed with 0.13 ml of a 4N solution of hydrogen chloride in dioxane and stirred for 18 hours at 60° C. After cooling, the mixture was admixed with a few drops of a sodium hydrogen carbonate solution and concentrated in a rotary evaporator. The resulting residue was purified by means of HPLC. This gave 65 mg (0.16 mmol; yield: 43%) of the product.

| System: | Waters Autopurification | | |
|---|---|---|---|
| Column: | XBridge C18 5μ 100 × 30 mm | | |
| Eluent A: | $H_2O$/0.1% HCOOH | | |
| Eluent B: | Acetonitrile | | |
| Gradient: | 0 min | 99% A | 1% B |
| | 1.00 min | 99% A | 1% B |
| | 7.50 min | 1% A | 99% B |
| | 10.00 min | 1% A | 99% B |
| Flow: | 50.0 ml/min | | |
| Detector: | DAD scan range 210-400 nm | | |
| | MS ESI+, ESI−, scan range 160-1000 m/z | | |
| Temperature: | Room temperature | | |

$^1$H NMR (400 MHz, DMSO): δ=10.57 (s, 1H), 8.58 (s, 1H), 7.93 (m, 2H), 7.82 (m, 2H), 5.51 (m, 1H), 3.52 (m, 2H), 3.26 (s, 3H), 3.14 (s, 3H), 1.30 (d, 3H).

EXAMPLE 13

(4-Methanesulphonylphenyl)(4-prop-2-ynyloxy-5-trifluoromethylpyrimidin-2-yl)amine

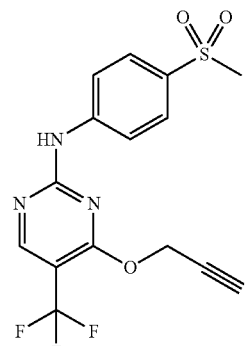

a) Preparation of the Intermediates

Compound 13.1

2-Chloro-4-prop-2-ynyloxy-5-trifluoromethylpyrimidine

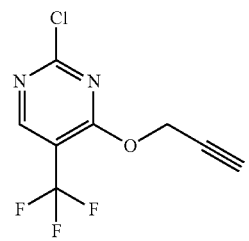

A solution of 2.00 g (9.2 mmol) of 2,4-dichloro-5-trifluoromethylpyrimidine and 0.71 ml (12.0 mmol) of prop-2-yn-1-ol in 24.4 ml of diethyl ether and 24.4 ml of acetonitrile was admixed at 0° C. with stirring in portions with 0.48 g of sodium hydride (55%). The mixture was slowly warmed to room temperature in an ice bath. After 3.5 hours, the mixture was admixed with ice and dilute sodium chloride solution. Extraction was carried out with ethyl acetate (2×). The combined organic phases were dried ($Na_2SO_4$), filtered and concentrated by evaporation. The resulting residue was purified by means of HPLC. This gave 0.29 g (1.2 mmol; yield: 13%) of the product.

| Column: | Chiralpak IA 5μ 250 × 30 mm |
|---|---|
| Eluent: | Hexane/ethanol 95:5 |
| Flow: | 40.0 ml/min |
| Detector: | DAD 210 nm |
| Temperature: | Room temperature |
| Retention time: | 4.8-5.3 min |

$^1$H NMR (400 MHz, DMSO): δ=8.91 (s, 1H), 5.18 (d, 2H), 3.71 (tr, 1H).

b) Preparation of the End Product 60 mg (0.25 mmol) of 2-chloro-4-prop-2-ynyloxy-5-trifluoromethylpyrimidine and 43 mg (0.25 mmol) of 4-methanesulphonylphenylamine in 1.8 ml of acetonitrile were admixed with 0.06 ml of a 4N solution of hydrogen chloride in dioxane and stirred for 18 hours at 60° C. The mixture was concentrated in a rotary evaporator and the resulting residue was purified by means of HPLC. This gave 29 mg (0.08 mmol, yield: 31%) of the product.

| System: | Waters Autopurification | | |
|---|---|---|---|
| Column: | XBridge C18 5μ 100 × 30 mm | | |
| Eluent A: | H$_2$O/0.1% HCOOH | | |
| Eluent B: | Acetonitrile | | |
| Gradient: | 0 min | 99% A | 1% B |
| | 1.00 min | 99% A | 1% B |
| | 7.50 min | 1% A | 99% B |
| | 10.00 min | 1% A | 99% B |
| Flow: | 50.0 ml/min | | |
| Detector: | DAD scan range 210-400 nm | | |
| | MS ESI+, ESI−, scan range | | |
| | 160-1000 m/z | | |
| Temperature: | Room temperature | | |

$^1$H NMR (400 MHz, DMSO): δ=10.71 (s, 1H), 8.64 (s, 1H), 7.98 (m, 2H), 7.82 (m, 2H), 5.16 (d, 2H), 3.68 (tr, 1H), 3.14 (s, 3H).

EXAMPLE 14

(4-Methanesulphonylphenyl)[5-trifluoromethyl-4-(3,3,3-trifluoropropoxy)pyrimidin-2-yl]amine

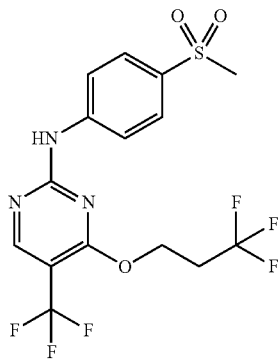 [SMILES: CS(=O)(=O)c1ccc(Nc2ncc(C(F)(F)F)c(OCCC(F)(F)F)n2)cc1]

A solution of 1.00 g (4.63 mmol) of 2,4-dichloro-5-trifluoromethylpyrimidine and 0.68 g (5.99 mmol) of 3,3,3-trifluoro-1-propanol in 12.2 ml of diethyl ether and 12.2 ml of acetonitrile was admixed at 0° C. with stirring in portions with 0.24 g of sodium hydride (55%). The mixture was slowly warmed to room temperature overnight in an ice bath. The mixture was admixed with ice and dilute sodium chloride solution. Extraction was carried out with ethyl acetate (2×). The combined organic phases were dried (Na$_2$SO$_4$), filtered and concentrated by evaporation. This gave 1.50 g of the crude product. 1.03 g of the crude product and 0.59 g (3.48 mmol) of 4-methanesulphonylphenylamine in 24.1 ml of acetonitrile were admixed with 0.87 ml of a 4N solution of hydrogen chloride in dioxane and stirred for 24 hours at 60° C. The mixture was admixed with a small amount of sodium hydrogen carbonate solution and concentrated in a rotary evaporator. The resulting residue was purified by means of HPLC. This gave 0.07 g (0.15 mmol) of the product.

| System: | Waters Autopurification | |
|---|---|---|
| Column: | XBridge C18 5μ 100 × 30 mm | |
| Eluent A: | H$_2$O/0.1% HCOOH | |
| Eluent B: | Acetonitrile | |
| Gradient: | 0-1 min | 30% B |
| | 1-7.5 min | 30-80% B |
| | 7.5-7.6 min | 80-99% B |
| | 7.6-10 min | 99% B |
| Flow: | 50.0 ml/min | |
| Detector: | DAD scan range 210-400 nm | |
| | MS ESI+, ESI−, scan range | |
| | 160-1000 m/z | |
| Temperature: | Room temperature | |
| Retention time: | 6.3-6.7 min | |

$^1$H NMR (400 MHz, DMSO): δ=10.66 (s, 1H), 8.65 (s, 1H), 7.99 (m, 2H), 7.88 (m, 2H), 4.72 (tr, 2H), 3.17 (s, 3H), 2.68 (m, 2H).

EXAMPLE 15

(4-Allyloxy-5-trifluoromethylpyrimidin-2-yl)(4-methane-sulphonylphenyl)amine

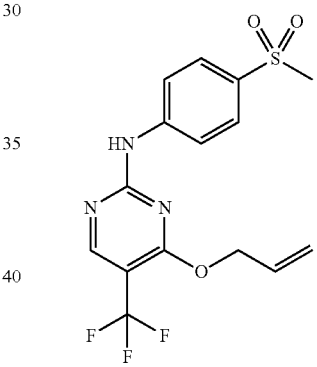

A solution of 1.00 g (4.63 mmol) of 2,4-dichloro-5-trifluoromethylpyrimidine and 0.41 ml (5.99 mmol) of 2-propen-1-ol in 12.2 ml of diethyl ether and 12.2 ml of acetonitrile was admixed at 0° C. with stirring in portions with 0.24 g of sodium hydride (55%). The mixture was slowly warmed to room temperature overnight in an ice bath. The mixture was admixed with ice and dilute sodium chloride solution. Extraction was carried out with ethyl acetate (2×). The combined organic phases were dried (Na$_2$SO$_4$), filtered and concentrated by evaporation. This gave 1.14 g of the crude product.

0.76 g of the crude product and 0.55 g (3.19 mmol) of 4-methanesulphonylphenylamine in 22.0 ml of acetonitrile were admixed with 0.80 ml of a 4N solution of hydrogen chloride in dioxane and stirred for 24 hours at 60° C. The mixture was admixed with a small amount of sodium hydrogen carbonate solution and concentrated in a rotary evaporator. The resulting residue was purified by means of HPLC. This gave 32 mg (0.09 mmol) of the product.

| System: | Waters Autopurification |
|---|---|
| Column: | XBridge C18 5μ 100 × 30 mm |

| | | |
|---|---|---|
| Eluent A: | H₂O/0.1% HCOOH | |
| Eluent B: | Acetonitrile | |
| Gradient: | 0-1 min | 30% B |
| | 1-7.5 min | 30-80% B |
| | 7.5-7.6 min | 80-99% B |
| | 7.6-10 min | 99% B |
| Flow: | 50.0 ml/min | |
| Detector: | DAD scan range 210-400 nm | |
| | MS ESI+, ESI−, scan range | |
| | 160-1000 m/z | |
| Temperature: | Room temperature | |
| Retention time: | 6.1-6.3 min | |

¹H NMR (400 MHz, DMSO): δ=10.61 (s, 1H), 8.61 (s, 1H), 7.95 (m, 2H), 7.83 (m, 2H), 6.04 (m, 1H), 5.38 (m, 1H), 5.27 (m, 1H), 5.02 (m, 2H), 3.14 (s, 3H).

EXAMPLE 16

(4-Cyclohexyloxy-5-trifluoromethylpyrimidin-2-yl)(4-methanesulphonylphenyl)amine

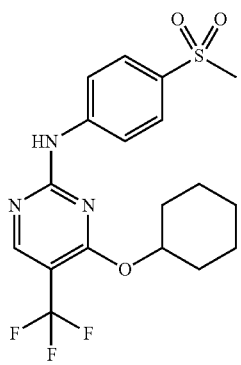

A solution of 1.00 g (4.63 mmol) of 2,4-dichloro-5-trifluoromethylpyrimidine and 0.64 ml (5.99 mmol) of cyclohexanol in 12.2 ml of diethyl ether and 12.2 ml of acetonitrile was admixed at 0° C. with stirring in portions with 0.24 g of sodium hydride (55%). The mixture was slowly warmed to room temperature overnight in an ice bath. The mixture was admixed with ice and dilute sodium chloride solution. Extraction was carried out with ethyl acetate (2×). The combined organic phases were dried (Na₂SO₄), filtered and concentrated by evaporation. This gave 1.30 g of the crude product. 0.65 g of the crude product and 0.40 g (2.3 mmol) of 4-methanesulphonylphenylamine in 16.0 ml of acetonitrile were admixed with 0.80 ml of a 4N solution of hydrogen chloride in dioxane and stirred for 24 hours at 60° C. The mixture was admixed with a small amount of sodium hydrogen carbonate solution and concentrated in a rotary evaporator. The resulting residue was purified by means of HPLC. This gave 0.05 g (0.12 mmol) of the product.

| | | | | |
|---|---|---|---|---|
| Column: | XBridge C18 5µ 100 × 30 mm | | | |
| Eluent A: | H₂O | | | |
| Eluent B: | Acetonitrile | | | |
| Gradient: | 0 min | 50% A | 50% B | |
| | 1.00 min | 50% A | 50% B | |
| | 7.50 min | 20% A | 80% B | |
| | 7.52 min | 1% A | 99% B | |
| | 10.00 min | 1% A | 99% B | |

| | |
|---|---|
| Flow: | 50.0 ml/min |
| Detector: | DAD scan range 210-400 nm |
| | MS ESI+, ESI−, scan range |
| | 160-1000 m/z |
| Temperature: | Room temperature |
| Retention time: | 6.2-6.5 min |

¹H NMR (400 MHz, DMSO): δ=10.56 (s, 1H), 8.57 (s, 1H), 7.95 (m, 2H), 7.82 (m, 2H), 5.24 (m, 1H), 3.14 (s, 3H), 1.91 (m, 2H), 1.53 (m, 8H).

Preparation of the Comparison Compounds

EXAMPLE C1

(2R,3R)-3-[2-(4-Cyclopropanesulphonylphenylamino)-5-trifluoromethylpyrimidin-4-ylamino]butan-2-ol

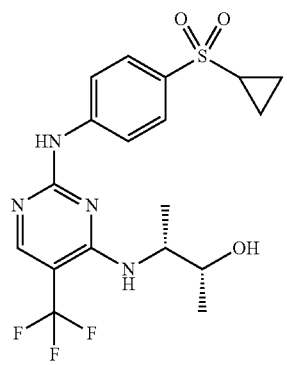 [SMILES: C[C@@H](O)[C@@H](C)Nc1nc(Nc2ccc(S(=O)(=O)C3CC3)cc2)ncc1C(F)(F)F]

Preparation of the End Product 566 mg (2.10 mmol) of (2R,3R)-3-(2-chloro-5-trifluoromethylpyrimidin-4-ylamino)butan-2-ol and 414 mg (2.10 mmol) of 4-methanesulphonylphenylamine in 10.2 ml of acetonitrile were admixed with 0.52 ml of a 4N solution of hydrogen chloride in dioxane and stirred for 17 hours at 60° C. The mixture was concentrated in a rotary evaporator and the resulting residue was purified chromatographically (DCM/ethanol 95:5). This gave 670 mg (1.56 mmol, yield: 74%) of the product.

¹H NMR (400 MHz, DMSO): δ=10.13 (s, 1H), 8.27 (s, 1H), 7.97 (m, 2H), 7.75 (m, 2H), 6.08 (d, 1H), 5.07 (d, 1H), 4.14 (m, 1H), 3.77 (m, 1H), 2.74 (m, 1H), 1.20 (d, 3H), 1.00 (m, 7H).

MS: 431 (ESI+)

EXAMPLE C2

(2R,3R)-3-[2-(4-Methanesulphonylphenylamino)-5-trifluoromethylpyrimidin-4-ylamino]butan-2-ol

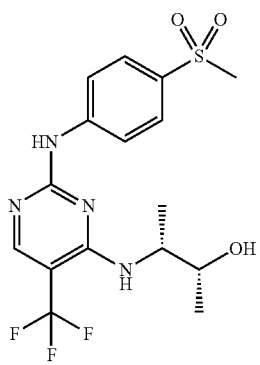

a) Preparation of the Intermediates

EXAMPLE C2.1

(2R,3R)-3-(2-Chloro-5-trifluoromethylpyrimidin-4-ylamino)butan-2-ol trifluoroacetate

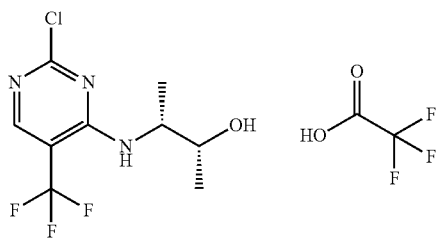 [SMILES: C[C@@H](O)[C@@H](C)Nc1nc(Cl)ncc1C(F)(F)F ; O=C(O)C(F)(F)F]

7.60 g (35.0 ml) of 2,4-dichloro-5-trifluoro-methylpyrimidine and 4.40 g (35.0 mmol) of (2R,3R)-3-aminobutan-2-ol hydrochloride in 139 ml of acetonitrile were admixed at 0° C. with stirring dropwise with 9.71 ml (70.0 mmol) of triethylamine. The mixture was slowly warmed to room temperature in an ice bath. After 3 days, the mixture was added to semi-concentrated sodium chloride solution. Extraction was carried out with ethyl acetate (2×). The combined organic phases were dried (Na$_2$SO$_4$), filtered and concentrated by evaporation. The resulting residue was purified by means of HPLC. This gave 2.49 g (6.5 mmol; yield: 19%) of the product.

| | |
|---|---|
| Column: | XBridge C18 5μ 100 × 30 mm |
| Eluent: | A: H$_2$O B: MeCN |
| Buffer: | A/0.1% TFA |
| Gradient: | 60% A + 40% B (2')_40 → 70% B (5, 5') → 99% B (0.1') |
| Flow: | 50.0 ml/min |
| Detector: | DAD (200-400 nm) TAC; MS-ESI+ (125-925 m/z) TIC |
| Temperature: | Room temperature |
| Retention time: | 3.1-3.8 min |

$^1$H NMR (400 MHz, DMSO): δ=8.38 (s, 1H), 6.73 (d, 1H), 4.07 (m, 1H), 3.71 (m, 1H), 1.12 (d, 3H), 1.01 (d, 3H).

b) Preparation of the End Products 84 mg (0.22 mmol) (2R,3R)-3-(2-chloro-5-trifluoro-methylpyrimidin-4-ylamino)butan-2-ol trifluoroacetate and 46 mg (0.22 mmol) of 4-methanesulphonylphenylamine hydrochloride in 1.4 ml of acetonitrile were admixed with 0.06 ml of a 4N solution of hydrogen chloride in dioxane and stirred at 50° C. After 19 hours, 21 mg (0.06 mmol) of (2R,3R)-3-(2-chloro-5-trifluoromethyl-pyrimidin-4-ylamino)butan-2-ol trifluoroacetate were again added and the mixture was stirred for a further 24 hours at 50° C. The mixture was concentrated in a rotary evaporator and the resulting residue was purified chromatographically (DCM/ethanol 95:5). This gave 42 mg (0.10 mmol, yield: 45%) of the product.

$^1$H NMR (400 MHz, DMSO): δ=10.13 (s, 1H), 8.26 (s, 1H), 7.96 (m, 2H), 7.78 (m, 2H), 6.08 (d, 1H), 5.07 (br, 1H), 4.14 (m, 1H), 3.76 (m, 1H), 3.12 (s, 3H), 1.20 (d, 3H), 1.05 (d, 3H).

MS: 405 (ESI+)

EXAMPLE C3

(R)-3-[2-(4-Methanesulphonylphenylamino) 5-trifluoro-methylpyrimidin-4-ylamino]-2-methylbutan-2-ol

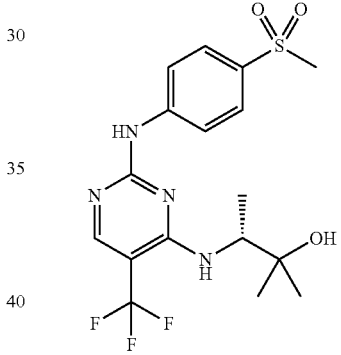

a) Preparation of the Intermediates

Compound C3.1

(R)-3-(2-Chloro-5-trifluoromethylpyrimidin-4-ylamino)-2-methylbutan-2-ol

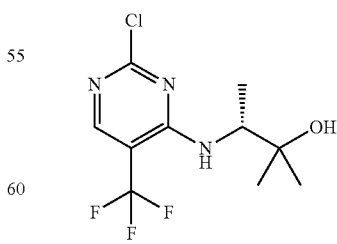

12.4 g (57.4 mmol) of 2,4-dichloro-5-trifluoro-methylpyrimidine and 5.90 g (57.3 mmol) of (R)-3-amino-2-methylbutan-2-ol in 227 ml of acetonitrile were admixed at 0° C. with stirring dropwise with 15.85 ml (114.4 mmol) of triethylamine. The mixture was slowly heated to room temperature in an ice bath. After 18 hours, the mixture was added to semiconcentrated sodium chloride solution. Extraction was carried out with ethyl acetate (2×). The combined organic phases were dried ($Na_2SO_4$), filtered and concentrated by evaporation. The resulting residue was purified by means of HPLC. This gave 6.39 g (22.5 mmol; yield: 39%) of the product.

| Column: | XBridge C18 5μ 105 × 30 mm | | |
|---|---|---|---|
| Eluent A: | $H_2O$/0.2% $NH_3$ | | |
| Eluent B: | Acetonitrile | | |
| Gradient: | 0 min | 99% A | 1% B |
| | 1.00 min | 99% A | 1% B |
| | 7.50 min | 1% A | 99% B |
| | 10.00 min | 1% A | 99% B |
| Flow: | 50.0 ml/min | | |
| Detector: | DAD scan range 200-400 nm | | |
| | MS ESI+, ESI−, scan range | | |
| | 120-1000 m/z | | |
| Temperature: | Room temperature | | |
| Retention time: | 6.9-8.3 min | | |

$^1$H NMR (400 MHz, DMSO): δ=8.45 (s, 1H), 6.55 (d, 1H), 5.00 (s, 1H), 4.11 (m, 1H), 1.14 (m, 9H).

b) Preparation of the End Product 199 mg (0.70 mmol) of (R)-3-(2-chloro-5-trifluoro-methylpyrimidin-4-ylamino)-2-methylbutan-2-ol and 146 mg (0.70 mmol) of 4-methanesulphonylphenylamine hydrochloride in 3.4 ml of acetonitrile were stirred for 16 hours at 60° C. The mixture was concentrated in a rotary evaporator and the resulting residue was purified chromatographically (DCM/ethanol 95:5). This gave 151 mg (0.36 mmol, yield: 51%) of the product.

$^1$H NMR (400 MHz, DMSO): δ=10.14 (s, 1H), 8.27 (s, 1H), 7.96 (m, 2H), 7.78 (m, 2H), 6.06 (d, 1H), 4.91 (br, 1H), 4.11 (m, 1H), 3.12 (s, 3H), 1.11 (m, 9H).

MS: 419(ESI+)

EXAMPLE 17

Assay 1

CDK1/CycB Kinase Assay

Recombinant CDK1 and CycB-GST fusion proteins, purified from baculovirus-infected insect cells (Sf9), were purchased from ProQinase GmbH, Freiburg. The histone IIIS used as kinase substrate is commercially available from Sigma.

CDK1/CycB (200 ng/measuring point) was incubated for 10 min at 22° C. in the presence of different concentrations of test substances (0 and within the range 0.001-10 μM) in assay buffer [50 mM Tris/HCl pH 8.0; 10 mM $MgCl_2$; 0.1 mM Na ortho-vanadate; 1.0 mM dithiothreitol; 0.5 μM adenosine trisphosphate (ATP); 10 μg/measuring point histone IIIS; 0.2 μCi/measuring point $^{33}$P-gamma ATP; 0.05% NP40; 1.25% dimethyl sulphoxide]. The reaction was stopped by adding EDTA solution (250 mM; pH 8.0; 15 μl/measuring point).

From each reaction mixture, 15 μl were applied to P30 filter strips (Wallac), and unincorporated $^{33}$P-ATP was removed by washing the filter strips three times, for 10 min in each case, in 0.5% phosphoric acid. After drying the filter strips for 1 hour at 70°, the filter strips were covered with scintillator strips (MeltiLex™ A, Wallac) and stoved for 1 hour at 90° C. The amount of incorporated $^{33}$P (substrate phosphorylation) was determined by scintillation measurement in a gamma-radiation measuring instrument (Wallac). The measured data were standardized to 0% inhibition (enzyme reaction without inhibitor) and 100% inhibition (all assay components except enzyme). The IC50 values were determined by means of a 4-parameter fit using the company's own software.

Assay 2: CDK2/CycE Kinase Assay

Recombinant CDK2 and CycE-GST fusion proteins, purified from baculovirus-infected insect cells (Sf9), were purchased from ProQinase GmbH, Freiburg. Histone IIIS, which was used as kinase substrate, was purchased from Sigma.

CDK2/CycE (50 mg/measuring point) was incubated for 10 min at 22° C. in the presence of different concentrations of test substances (0 μM, and within the range 0.001-10 μM) in assay buffer [50 mM Tris/HCl pH 8.0; 10 mM $MgCl_2$; 0.1 mM Na ortho-vanadate; 1.0 mM dithiothreitol; 0.5 μM adenosine trisphosphate (ATP); 10 μg/measuring point histone IIIS; 0.2 μCi/measuring point $^{33}$P-gamma ATP; 0.05% NP40; 1.25% dimethyl sulphoxide]. The reaction was stopped by adding EDTA solution (250 mM; pH 8.0; 15 μl/measuring point).

From each reaction mixture, 15 μl were applied to P30 filter strips (Wallac), and unincorporated $^{33}$P-ATP was removed by washing the filter strips three times, for 10 min in each case, in 0.5% phosphoric acid. After drying the filter strips for 1 hour at 70° C., the filter strips were covered with scintillator strips (MeltiLex™ A, Wallac) and stoved for 1 hour at 90° C. The amount of incorporated $^{33}$P (substrate phosphorylation) was determined by scintillation measurement in a gamma-radiation measuring instrument (Wallac). The measured data were standardized to 0% inhibition (enzyme reaction without inhibitor) and 100% inhibition (all assay components except enzyme). The IC50 values were determined by means of a 4-parameter fit using the company's own software.

Assay 3: CDK4/CycD Kinase Assay

Recombinant CDK4 and CycD1-GST fusion proteins, purified from baculovirus-infected insect cells (Sf9), were purchased from ProQinase GmbH, Freiburg. CDK4/CycD1 (250 ng/measuring point) was incubated for 3 hours at 22° C. in the presence of different concentrations of test substances (0 μM, and within the range 0.001-10 μM) in 31 μl of assay buffer [50 mM Hepes pH 7.0; 2.5 mM MnCl; 0.05 mM Na ortho-vanadate; 1.0 mM dithiothreitol; 0.25 μM adenosine trisphosphate (ATP); 0.5 μM biotinylated myelin basic protein (bio-MPB, GE Healthcare); 0.05 μCi/measuring point $^{33}$P-gamma ATP; 0.005% NP40; 0.025% bovine serum albumin; 3% dimethyl sulphoxide]. The reaction was stopped by adding 50 μl of stop-mix [100 μM ATP; 10 mM EDTA pH 8.0; 0.2% Triton X100; 0.125 mg of streptavidin-SPA Beads (GE Healthcare)]. After incubation for 10 min at room temperature, the SPA beads were pelleted by centrifugation (10 min; 1500 g). The amount of incorporated $^{33}$P (substrate phosphorylation) was determined by scintillation measurement in a beta-radiation measuring instrument (Microbeta, Perkin Elmer). The measured data were standardized to 0% inhibition (enzyme reaction without inhibitor) and 100% inhibition (all assay components except enzyme). The IC50 values were determined by means of a 4-parameter fit using the company's own software.

Assay 4: VEGF Receptor-2 Kinase Assay

Recombinant VEGF receptor tyrosine kinase-2 was purified as GST fusion protein from baculovirus-infected insect cells (Sf9). Poly-(Glu4Tyr), which was used as kinase substrate, was purchased from Sigma.

VEGF receptor tyrosine kinase (90 ng/measuring point) was incubated for 10 min at 22° C. in the presence of different concentrations of test substances (0 μM, and within the range 0.001-10 µM) in 30 µl of assay buffer [40 mM Tris/HCl pH 5.5; 10 mM $MgCl_2$; 1 mM $MnCl_2$; 3 µM Na ortho-vanadate; 1.0 mM dithiothreitol; 8 µM adenosine trisphosphate (ATP); 0.96 µg/measuring point poly-($Glu_4Tyr$); 0.2 µCi/measuring point $^{33}$P-gamma ATP; 1.4% dimethyl sulphoxide]. The reaction was stopped by adding EDTA solution (250 mM; pH 8.0; 15 µl/measuring point).

From each reaction mixture, 15 µl were applied to P30 filter strips (Wallac), and unincorporated $^{33}$P-ATP was removed by washing the filter strips three times, for 10 min in each case, in 0.5% phosphoric acid. After drying the filter strips for 1 hour at 70° C., the filter strips were covered with scintillator strips (MeltiLex™ A, Wallac) and stoved for 1 hour at 90° C. The amount of incorporated $^{33}$P (substrate phosphorylation) was determined by scintillation measurement in a gamma-radiation measuring instrument (Wallac). The measured data were standardized to 0% inhibition (enzyme reaction without inhibitor) and 100% inhibition (all assay components except enzyme). The IC50 values were determined by means of a 4-parameter fit using the company's own software.

Assay 5: Proliferation Assays

Cultivated human tumour cells (MCF7, hormone-independent human breast carcinoma cells, acquired from ATCC HTB22; NCI-H460, human non-small-cell lung carcinoma cells, ATCC HTB-177; DU 145, hormone-independent human prostate carcinoma cells, ATCC HTB-81; HeLa-MaTu, human cervix carcinoma cells, EPO-GmbH, Berlin; HeLa-MaTu-MDR, multiple drug-resistant human cervix carcinoma cells, EPO-GmbH, Berlin; Caco-2, human colon carcinoma cells, ATCC HTB-37; B16F10, murine melanoma cell, ATCC CRL-6475) were plated out at a density of ca. 1000-5000 cells/measuring point, depending on the growth rate of the particular cells, in a 96-well multititre plate in 200 µl of the corresponding growth medium. After 24 hours, the cells of one plate (zero-point plate) were stained with crystal violet (see below), whereas the medium of the other plates was replaced with fresh culture medium (200 µl), to which the test substances had been added at different concentrations (0 µM, and in the range 0.003-3 µM; the final concentration of the solvent dimethyl sulphoxide was 0.5%). The cells were incubated for 4 days in the presence of the test substances. Cell proliferation was determined by staining the cells with crystal violet: the cells were fixed by adding 20 µl/measuring point of an 11% glutaraldehyde solution for 15 min at room temperature. After washing the fixed cells with water three times, the plates were dried at room temperature. The cells were stained by adding 100 µl/measuring point of a 0.1% crystal violet solution (pH adjusted to pH 3 by adding acetic acid). After washing the stained cells with water three times, the plates were dried at room temperature. The dye was dissolved by adding 100 µl/measuring point of a 10% acetic acid solution. The extinction was determined photometrically at a wavelength of 595 nm. The measured data were standardized to 0% inhibition [untreated (0 µM) cells] and 100% inhibition (extinction values of the zero-point plate). The IC50 values were determined by means of a 4-parameter fit using the company's own software.

Assay 6: Permeability Assays

The Caco-2 monolayer is a barrier between 2 compartments. The cells here behave similarly to the small intestine cells. Active ingredients can be transported either paracellularly or transcellularly. Here, the transport takes place in most cases from apical (luminal) to basolateral (serosal). In the case of p-glycoprotein substrates, back-transport from basolateral to apical is also usually observed.

Experimental procedure: The permeability test is carried out both from apical to basolateral and also from basolateral to apical. For this, two filters are used per substance; incubation takes place over 90 min at 37° C. in a water bath. Besides the bidirectional permeability of test and reference substances (references: low permeability: PEG 4000; high permeability: clonidine; directional permeability: digoxin), the integrity of the cell monolayer is ensured by determining the transepithelial resistance (TEER). As reference substances, (i) PEG 4000 are used as hydrophilic marker. On account of its high molecular weight, it is unable to permeate into the cell membrane or into the pores of the tight junctions. PEG 4000 is therefore a marker of the intactness of the cell monolayer and the narrowness of the tight junctions. PEG 4000 is not absorbed in humans. (ii) Clonidine is known as completely absorbed substances in people (100%). They serve as markers for very highly permeable substances with Papp values above 100 nm/s. (iii) Digoxin is a known Pgp substrate. It exhibits a low permeability from apical to basolateral. In the reverse experiment (basolateral to apical), the Papp values should be higher by a factor of about 10 as a result of the active directional transport into the apical compartment.

Evaluation: The permeation coefficient (Papp) is calculated via the substance concentration on the donor side and receptor side according to the following formula:

$$Papp = (Vc\ res/A \cdot CO_{t0,don}) \cdot (\text{delta}\ C_{res}/\text{delta}\ T),$$

where

Vres: Buffer volume on the receptor side,

A: Filter area=1 $cm^2$, $C_{t0,don}$: Substance concentration on the donor side at time point 0, delta $C_{res}$/delta T: Change in substance concentration over time on the receptor side.

The permeation coefficient Papp is used to estimate the absorption in people according to the following scheme:

| Permeation coefficient Papp [nm/s] | Estimated absorption |
| --- | --- |
| >1/<10 | Poor absorption, preferably paracellular via the tight junctions (examples: mannitol, sucrose, cimetidine) |
| >10/<60 | Average absorption, preferably transcellular |
| >60/>100 | Good absorption, preferably transcellular (examples: clonidine, testosterone) |

Results from the Enzyme and Cell Assays

TABLE 1

Results of the enzyme assays

| Ex. | CDK1/CycB (Assay 1) | CDK2/CycE (Assay 2) | CDK4/CycD (Assay 3) | VEGF-R2 (Assay 4) |
| --- | --- | --- | --- | --- |
|  | Concentration of the half-maximal inhibition of the enzyme activity, IC50 [nM] | | | |
| 1 | 16 | 16 | 20 | 260 |
| 2 | 9 | 8 | 24 | 480 |
| 3 | 32 | 12 | 78 | 490 |
| 4 | 36 | 21 |  | 180 |
| 5 | 41 | 36 |  | 350 |
| 6 | 24 | 12 |  | 430 |
| 7 | 23 | 21 |  | 230 |
| 8 | 43 | 11 |  | 460 |
| 9 | 12 | 6 |  | 170 |
| 10 | 82 | 43 |  | 200 |
| 11 | 3 | 3 |  | 170 |

TABLE 1-continued

Results of the enzyme assays

| Ex. | CDK1/CycB (Assay 1) | CDK2/CycE (Assay 2) | CDK4/CycD (Assay 3) | VEGF-R2 (Assay 4) |
|---|---|---|---|---|
| | Concentration of the half-maximal inhibition of the enzyme activity, IC50 [nM] | | | |
| 12 | 51 | 12 | | 400 |
| 13 | 130 | 25 | | 610 |
| 14 | 740 | 94 | | >1000 |
| 15 | 280 | 49 | | 850 |
| 16 | >1000 | 480 | | 890 |
| Structure 692 of Example 1 from WO 2003/032997 | 53 | 55 | >1000 | 120 |
| Comparative Example C1 | 8 | 6 | 52 | 51 |
| Comparative Example C2 | 4 | 4 | 35 | 92 |
| Comparative Example C3 | 9 | 8 | 24 | 190 |

TABLE 2

Results of the proliferation assay (Assay 5)

| Ex. | HeLa-MaTu | HeLa MaTu-ADR | MCF7 | NCI-H460 | DU145 | Caco-2 | B16F10 |
|---|---|---|---|---|---|---|---|
| | Concentration of the half-maximal inhibition of the cell proliferation, IC50 [nM] | | | | | | |
| 1 | 11 | 9 | 23 | 41 | 17 | 45 | 49 |
| 2 | 14 | 14 | 35 | 38 | 34 | 66 | 70 |
| 3 | 35 | 39 | 160 | 140 | 74 | 180 | 270 |
| 4 | | 142 | 105 | 226 | 194 | 205 | 287 |
| 12 | | | 191 | | | | |
| 13 | | | 740 | | | | |
| 14 | | | 2200 | | | | |
| 15 | | | 1500 | | | | |
| 16 | | | 1400 | | | | |
| Structure 692 of Example 1 from WO 2003/032997 | 150 | 1200 | 71 | 290 | 510 | 1400 | 450 |
| Comparative Example C1 | | 26 | 65 | 37 | 46 | 63 | 78 |
| Comparative Example C2 | | 32 | 43 | 34 | 75 | 76 | 89 |
| Comparative Example C3 | | 37 | 61 | 93 | 60 | 133 | 106 |

TABLE 3

Results of the permeability assay (Assay 6)

| Ex. | apical-basolateral (a-b) Permeation coefficient, Papp [nM/s] | basolateral-apical (b-a) [nM/s] | ratio (b-a)/(a-b) |
|---|---|---|---|
| 1 | 165 | 147 | 0.9 |
| 2 | 196 | 194 | 1.0 |
| Structure 692 of Example 1 from WO 2003/032997 | 9 | 294 | 32 |
| Comparative Example C1 | 207 | 174 | 0.8 |
| Comparative Example C2 | 180 | 178 | 1.0 |

CONCLUSIONS FROM THE ENZYME AND CELL ASSAYS

The example compounds 1-3 exhibit a 2- to 6-fold greater inhibition of the activity of cyclin-dependent kinase CDK1 and a 3- to 7-fold greater inhibition of CDK2 compared to structure 692 of Example 1 from WO 2003/032997 (Tab. 1). The example compounds 1-3 exhibit a potent inhibition of CDK4 at nanomolar concentrations whereas structure 692 of Example 1 from WO 2003/032997 has still not reached the half-maximal inhibition of the CDK4 activity at a concentration of 1000 nM. At the same time, the selectivity with regard to the CDK inhibition compared with the inhibition of the VEGF receptor kinase-2 (VEGF-R2) is clearly increased for Examples 1-3 (15- to 50-fold greater inhibition of the CDKs), whereas structure 692 of Example 1 from WO 2003/032997 has only a ca. 2-fold selectivity. In the cell proliferation assays, the example compounds 1-3 exhibit the 50% inhibition of the proliferation at considerably lower concentrations than structure 692 of Example 1 from WO 2003/032997 (Tab. 2, exception: Ex. 2 on MCF7 cells). Surprisingly, this effect is particularly marked for the cell lines DU145, Caco-2, HeLa-MaTu-ADR, and B16F10 (up to 130-fold better antiproliferative activity of the example compounds 1-3 compared with structure 692 of Example 1 from WO 2003/032997). The permeability assays (Tab. 3) show that the example compounds 1-2 have good and free permeation via a closed Caco-2 cell layer. Structure 692 of Example 1 from WO 2003/032997 is characterized by a very poor permeation in the absorptive direction and by a high permeation in the efflux direction.

Direct comparison of Examples 1-3 with the analogous 4-N compounds (Comparative Examples C1-C3) reveals an improvement in the kinase selectivity of example compounds 1-3 compared with the VEGF receptor kinase-2 by a factor of at least 2. Compared with the comparative examples, the example compounds 1-2 exhibit an improvement in the inhibition of CDK4 and, on the cell lines DU145 and HeLa-MaTu-ADR, exhibit an antiproliferative effect which is increased by more than a factor of 2.

This data demonstrates the superiority of the compounds according to the invention (Examples 1-3) compared with the closest prior art (WO 2003/032997). This is shown particularly clearly by reference to the increased antiproliferative activity of the example compounds in the cell lines DU145, HeLa-MaTu-ADR and Caco-2 known to be chemotherapy-resistant.

The invention claimed is:

1. Compounds of formula (I), (I)

[Structure: 4-[(5-trifluoromethyl-4-OR²-pyrimidin-2-yl)amino]phenyl sulfonyl R¹]

in which
- $R^1$ is $C_1$-$C_6$-alkyl, $C_2$-$C_6$-alkenyl, $C_2$-$C_6$-alkynyl, $C_3$-$C_7$-cycloalkyl or phenyl, in each case optionally substituted one or more times, identically or differently, with hydroxy, —$NR^3R^4$, cyano, halogen, —$CF_3$, $C_1$-$C_6$-alkoxy, —$OCF_3$ or $C_1$-$C_6$-alkyl,
- $R^2$ is $C_1$-$C_{10}$-alkyl, $C_3$-$C_{10}$-alkenyl, $C_3$-$C_{10}$-alkynyl or $C_3$-$C_7$-cycloalkyl,
  in each case optionally substituted one or more times, identically or differently, with
  a) halogen, hydroxy, —$NR^3R^4$, cyano, —$CF_3$, or —$OCF_3$, or
  b) $C_1$-$C_6$-alkoxy, $C_1$-$C_6$-alkyl, $C_2$-$C_6$-alkenyl, $C_2$-$C_6$-alkynyl, $C_3$-$C_8$-cycloalkyl, —O—$CH_2$-phenyl, or $C_n$-alkoxycarbonyl,
  in each case optionally substituted themselves one or more times, identically or differently, with halogen, hydroxy, $C_1$-$C_6$-alkyl, $C_1$-$C_6$-alkoxy, —$NR^3R^4$, —$CF_3$ or —$OCF_3$,
- $R^3$ and $R^4$ independently of one another, are hydrogen, $C_1$-$C_6$-alkyl, $C_2$-$C_6$-alkenyl, $C_3$-$C_8$-cycloalkyl, phenyl, heterocyclyl having 3 to 8 ring atoms, or monocyclic heteroaryl, optionally substituted one or more times, identically or differently, with hydroxy, —$NR^5R^6$, cyano, halogen, —$CF_3$, $C_1$-$C_6$-alkoxy or $OCF_3$, or
- $R^3$ and $R^4$ together with the nitrogen atom, form a 5- to 7-membered ring which, optionally, in addition to the nitrogen atom, contains one or two further heteroatoms and which may be substituted one or more times, identically or differently, with hydroxy, —$NR^5R^6$, cyano, halogen, —$CF_3$, $C_1$-$C_6$-alkoxy or —$OCF_3$, and
- $R^5$ and $R^6$ independently of one another, are hydrogen or $C_1$-$C_6$-alkyl, which is optionally substituted one or more times, identically or differently, with hydroxy, cyano, halogen, —$CF_3$, $C_1$-$C_6$-alkoxy or —$OCF_3$, and salts, diastereomers and enantiomers thereof.

2. Compounds according to claim 1,
where
$R^1$ is $C_1$-$C_6$-alkyl, $C_2$-$C_6$-alkenyl, $C_2$-$C_6$-alkynyl, $C_3$-$C_7$-cycloalkyl or phenyl, in each case optionally substituted one or more times, identically or differently, with hydroxy, cyano, halogen, —$CF_3$, $C_1$-$C_6$-alkoxy, —$OCF_3$ or $C_1$-$C_6$-alkyl,
and salts, diastereomers and enantiomers thereof.

3. Compounds according to claim 1,
where
$R^2$ is $C_1$-$C_{10}$-alkyl, $C_3$-$C_{10}$-alkenyl, $C_3$-$C_{10}$-alkynyl radical or a $C_3$-$C_7$-cycloalkyl ring,
in each case optionally substituted one or more times, identically or differently, with halogen, hydroxy, cyano, —$CF_3$, —$OCF_3$, or $C_1$-$C_6$-alkoxy, $C_1$-$C_6$-alkyl, in each case optionally substituted themselves one or more times, identically or differently, with halogen or hydroxy,
and salts, diastereomers and enantiomers thereof.

4. Compounds according to claim 1,
wherein
$R^1$ is $C_1$-$C_6$-alkyl, $C_2$-$C_6$-alkenyl, $C_3$-$C_7$-cycloalkyl or phenyl, in each case optionally substituted one or more times, identically or differently, with hydroxy, cyano, halogen or $C_1$-$C_6$-alkyl,
and salts, diastereomers and enantiomers thereof.

5. Compounds according to claim 1,
where
$R^2$ is $C_2$-$C_6$-alkyl, $C_3$-$C_6$-alkenyl, $C_3$-$C_6$-alkynyl or $C_3$-$C_7$-cycloalkyl, which is optionally substituted one or more times with hydroxy, halogen, —$CF_3$ or $C_1$-$C_3$-alkoxy,
and salts, diastereomers and enantiomers thereof.

6. Compounds according to claim 1,
where
$R^2$ has the formula ($I_{R^2}$), ($I_{R^2}$)

[Structure with $R^a$, $R^b$, $R^c$ and OH]

in which
$R^a$ is methyl, ethyl, propyl or isopropyl, and
$R^b$ and $R^c$ independently of one another, are hydrogen, methyl or ethyl,
and salts, diastereomers and enantiomers thereof.

7. Compounds according to claim 6,
where
$R^a$ and $R^b$ are methyl and $R^c$ is hydrogen or methyl, and salts, diastereomers and enantiomers thereof.

8. Compounds of formula (Ia)

(Ia)

[Structure]

in which
$R^1$ is methyl or cyclopropyl,
$R^a$ and $R^b$ are methyl group, and
$R^c$ is hydrogen or methyl,
and salts, diastereomers and enantiomers thereof.

9. Process for the preparation of the compounds according to claim 1, comprising at least one of the steps a1) functionalization of the 4-position of 2,4-dichloro-5-iodopyrimidine (1)

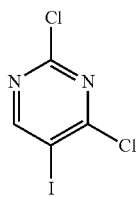
(1)

by reaction with an alcohol of formula (2)

(2)

to form an intermediate of formula (3),

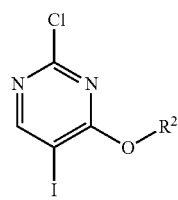
(3)

and subsequent reaction of the intermediate of formula (3) to form the 5-$CF_3$ intermediate (4)

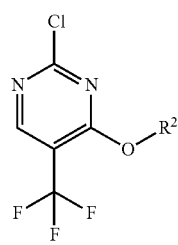
(4)

or alternatively
a2) direct reaction of 2,4-dichloro-5-trimethylpyrimidine (5)

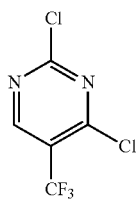
(5)

and an alcohol of formula (2)

(2)

to form the 5-$CF_3$ intermediate (4),

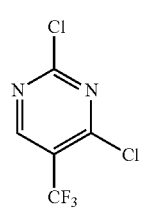
(5)

b) oxidation of a thioether of formula (7)

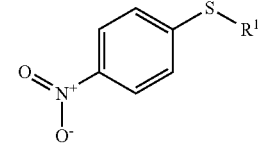
(7)

to give the sulphone of formula (8),

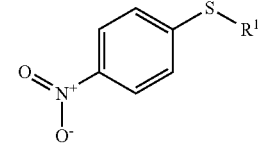
(7)

c) reduction of the compound of formula (8)

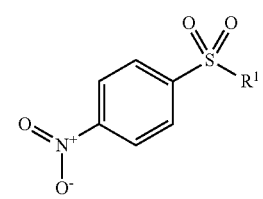
(8)

to a compound of the formula (9),

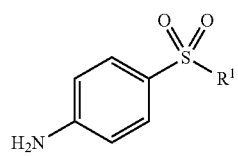
(9)

d) coupling of the compound of formula (4)

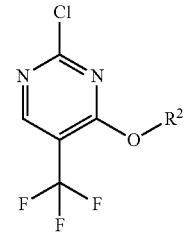
(4)

and the compound of formula (9)

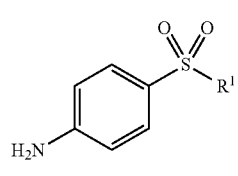
(9)

to yield a compound of formula (1)

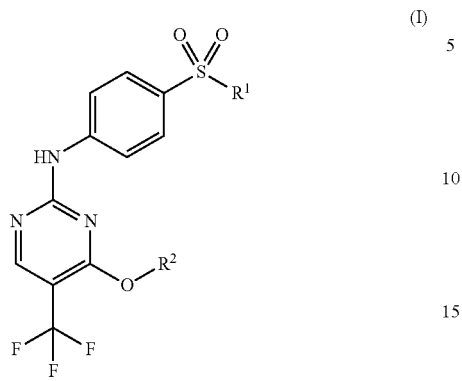

where the substituents $R^1$ and $R^2$ have the meanings given in claim 1.

10. Compounds according to claim 1 for use as medicament.

11. A method for producing a medicament for the treatment of cancer which comprises formulating a compound of claim 1 into a pharmaceutically acceptable composition.

12. Pharmaceutical formulation comprising a compound according to claim 1 and a pharmaceutically acceptable excipient.

* * * * *